US012694512B2

(12) United States Patent
Kumar et al.

(10) Patent No.: US 12,694,512 B2
(45) Date of Patent: Jul. 28, 2026

(54) SYSTEMS AND METHODS FOR AI-ASSISTED SURGERY

(71) Applicant: KALIBER LABS INC., San Francisco, CA (US)

(72) Inventors: Bipul Kumar, San Francisco, CA (US); Biswajit Dev Sarma, San Francisco, CA (US); Chandra Jonelagadda, San Francisco, CA (US); Mark Ruiz, San Francisco, CA (US); Ray Rahman, San Francisco, CA (US)

(73) Assignee: Kaliber Labs Inc., San Francisco, CA (US)

( * ) Notice: Subject to any disclaimer, the term of this patent is extended or adjusted under 35 U.S.C. 154(b) by 772 days.

(21) Appl. No.: 17/918,873

(22) PCT Filed: Apr. 13, 2021

(86) PCT No.: PCT/US2021/027109
§ 371 (c)(1),
(2) Date: Oct. 13, 2022

(87) PCT Pub. No.: WO2021/211603
PCT Pub. Date: Oct. 21, 2021

(65) Prior Publication Data
US 2023/0245753 A1 Aug. 3, 2023

Related U.S. Application Data

(60) Provisional application No. 63/143,367, filed on Jan. 29, 2021, provisional application No. 63/030,695, filed on May 27, 2020.

(30) Foreign Application Priority Data

Apr. 13, 2020 (IN) .............................. 202041015990

(51) Int. Cl.
*G06T 7/00* (2017.01)
*G06V 10/77* (2022.01)
(Continued)

(52) U.S. Cl.
CPC ........ *G06T 7/0012* (2013.01); *G06V 10/7715* (2022.01); *G06V 10/774* (2022.01);
(Continued)

(58) Field of Classification Search
CPC ...... G06T 7/0012; G16H 20/40; G06V 20/70; G06V 10/7715; G06V 10/809; G06V 10/82; G06V 10/774
See application file for complete search history.

(56) References Cited

U.S. PATENT DOCUMENTS 4,600,005 A 7/1986 Hendel
5,215,095 A 6/1993 Macvicar et al.
(Continued)

FOREIGN PATENT DOCUMENTS

EP 2194836 B1 11/2015
JP 2002065585 A 3/2002
(Continued)

OTHER PUBLICATIONS

Buslaev et al.; Albumentations: Fast and flexible image augmentations; Information; 11(2); 125; doi:10.33990/info11020125; 20 pages; Feb. 2020.
(Continued)

*Primary Examiner* — Mohammed H Zuberi
(74) *Attorney, Agent, or Firm* — Shay Glenn LLP

(57) ABSTRACT

Various embodiments of the invention provide systems and methods to assist or guide an arthroscopic surgery or other surgical procedure e.g., surgery of the shoulder, knee or hip. The method comprises steps of receiving an image from an interventional imaging device, identifying a feature in the
(Continued)

image using an image recognition algorithm, overlaying the features on a video feed on a display device and making recommendations or suggestions to an operator based on the identified feature in the image.

22 Claims, 15 Drawing Sheets

(51) Int. Cl.

| | |
|---|---|
| *G06V 10/774* | (2022.01) |
| *G06V 10/80* | (2022.01) |
| *G06V 10/82* | (2022.01) |
| *G06V 20/70* | (2022.01) |
| *G16H 20/40* | (2018.01) |

(52) U.S. Cl.
CPC ............ *G06V 10/809* (2022.01); *G06V 10/82* (2022.01); *G06V 20/70* (2022.01); *G16H 20/40* (2018.01); *G06T 2207/20081* (2013.01); *G06T 2207/20084* (2013.01); *G06T 2207/30004* (2013.01); *G06V 2201/034* (2022.01)

(56) References Cited

U.S. PATENT DOCUMENTS

| | | | |
|---|---|---|---|
| 6,491,699 | B1 | 12/2002 | Henderson et al. |
| 8,860,757 | B2 | 10/2014 | Duhamel et al. |
| 9,075,899 | B1* | 7/2015 | Reicher .................. G16H 30/20 |
| 10,130,429 | B1 | 11/2018 | Weir |
| 10,169,535 | B2* | 1/2019 | Mentis ................. A61B 1/0005 |
| 10,543,046 | B2 | 1/2020 | Charron et al. |
| 10,806,325 | B2 | 10/2020 | Miller et al. |
| 11,832,996 | B2* | 12/2023 | Shelton, IV ........... G16H 30/40 |
| 2003/0181810 | A1 | 9/2003 | Murphy et al. |
| 2003/0195883 | A1 | 10/2003 | Mojsilovic et al. |
| 2004/0087852 | A1 | 5/2004 | Chen |
| 2004/0199404 | A1 | 10/2004 | Ripperger et al. |
| 2006/0058616 | A1 | 3/2006 | Marquart et al. |
| 2006/0258938 | A1 | 11/2006 | Hoffman et al. |
| 2007/0016009 | A1 | 1/2007 | Lakin et al. |
| 2007/0116036 | A1 | 5/2007 | Moore |
| 2007/0168461 | A1 | 7/2007 | Moore |
| 2009/0088897 | A1 | 4/2009 | Zhao et al. |
| 2009/0317002 | A1 | 12/2009 | Dien |
| 2010/0249507 | A1 | 9/2010 | Prisco et al. |
| 2011/0190774 | A1 | 8/2011 | Nikolchev et al. |
| 2011/0202370 | A1 | 8/2011 | Green, III et al. |
| 2011/0301447 | A1 | 12/2011 | Park et al. |
| 2012/0130258 | A1 | 5/2012 | Taylor et al. |
| 2012/0226150 | A1 | 9/2012 | Balicki et al. |
| 2012/0289782 | A1 | 11/2012 | Viola |
| 2013/0073310 | A1 | 3/2013 | Awdeh |
| 2013/0096373 | A1 | 4/2013 | Chabanas et al. |
| 2013/0211232 | A1 | 8/2013 | Murphy et al. |
| 2014/0058406 | A1 | 2/2014 | Tsekos |
| 2014/0149407 | A1 | 5/2014 | Qian et al. |
| 2014/0216966 | A1 | 8/2014 | Ramkhelawan et al. |
| 2014/0236159 | A1 | 8/2014 | Haider et al. |
| 2014/0267658 | A1 | 9/2014 | Speier et al. |
| 2015/0005622 | A1 | 1/2015 | Zhao et al. |
| 2015/0161802 | A1 | 6/2015 | Christiansen |
| 2015/0221105 | A1 | 8/2015 | Tripathi et al. |
| 2015/0332196 | A1 | 11/2015 | Stiller et al. |
| 2016/0000515 | A1 | 1/2016 | Sela et al. |
| 2016/0151117 | A1 | 6/2016 | Gibbs et al. |
| 2016/0259888 | A1 | 9/2016 | Liu et al. |
| 2016/0270641 | A1 | 9/2016 | Mirza et al. |
| 2016/0378861 | A1 | 12/2016 | Eledath et al. |
| 2017/0007327 | A1 | 1/2017 | Haider et al. |
| 2017/0060867 | A1 | 3/2017 | Moutinho |
| 2017/0151022 | A1 | 6/2017 | Jascob et al. |
| 2017/0193160 | A1* | 7/2017 | Long ...................... G16H 50/50 |

| | | | |
|---|---|---|---|
| 2018/0049622 | A1* | 2/2018 | Ryan ...................... A61B 34/20 |
| 2018/0071032 | A1 | 3/2018 | de Almeida Barreto |
| 2018/0122506 | A1 | 5/2018 | Grantcharov et al. |
| 2018/0168740 | A1 | 6/2018 | Ryan et al. |
| 2018/0204111 | A1 | 7/2018 | Zadeh et al. |
| 2018/0247128 | A1* | 8/2018 | Alvi ........................ H04L 67/12 |
| 2018/0249888 | A1 | 9/2018 | Kucharski et al. |
| 2018/0366231 | A1 | 12/2018 | Wolf et al. |
| 2018/0368656 | A1 | 12/2018 | Austin et al. |
| 2019/0069957 | A1* | 3/2019 | Barral .................... A61B 34/20 |
| 2019/0192232 | A1 | 6/2019 | Altmann et al. |
| 2019/0209080 | A1 | 7/2019 | Gullotti et al. |
| 2019/0311493 | A1* | 10/2019 | Hillborg .............. G06V 10/764 |
| 2019/0362834 | A1* | 11/2019 | Venkataraman ....... G06V 20/41 |
| 2019/0380792 | A1 | 12/2019 | Poltaretskyi et al. |
| 2019/0385302 | A1 | 12/2019 | Ngo Dinh et al. |
| 2020/0005949 | A1 | 1/2020 | Warkentine |
| 2020/0078123 | A1 | 3/2020 | Venkataraman et al. |
| 2020/0107002 | A1 | 4/2020 | Casas |
| 2020/0111564 | A1 | 4/2020 | Mastros |
| 2020/0197098 | A1 | 6/2020 | Chopra et al. |
| 2020/0210769 | A1* | 7/2020 | Hou ...................... G06F 18/211 |
| 2020/0211720 | A1* | 7/2020 | Goldberg ............... G16H 10/60 |
| 2020/0237452 | A1* | 7/2020 | Wolf ...................... G06F 3/048 |
| 2020/0265273 | A1 | 8/2020 | Wei et al. |
| 2020/0273575 | A1 | 8/2020 | Wolf et al. |
| 2020/0394499 | A1 | 12/2020 | Yao et al. |
| 2021/0059758 | A1 | 3/2021 | Avendi et al. |
| 2021/0128244 | A1 | 5/2021 | Couture et al. |
| 2021/0192759 | A1 | 6/2021 | Lang |
| 2021/0196382 | A1 | 7/2021 | Mumaw et al. |
| 2021/0196398 | A1 | 7/2021 | Ye et al. |
| 2021/0256719 | A1 | 8/2021 | Hufford et al. |
| 2021/0298869 | A1 | 9/2021 | Wolf et al. |
| 2021/0307841 | A1 | 10/2021 | Buch et al. |
| 2021/0327567 | A1 | 10/2021 | Fine et al. |
| 2021/0338331 | A1 | 11/2021 | Quaid, III |
| 2021/0338342 | A1 | 11/2021 | Abhari et al. |
| 2022/0031402 | A1* | 2/2022 | Ye ....................... A61G 13/0018 |
| 2022/0079675 | A1 | 3/2022 | Lang |
| 2022/0087746 | A1 | 3/2022 | Lang |
| 2022/0104694 | A1 | 4/2022 | Shelton, IV et al. |
| 2022/0122263 | A1 | 4/2022 | Yang |
| 2022/0165403 | A1 | 5/2022 | Asselmann et al. |
| 2022/0207896 | A1* | 6/2022 | Fouts ................... G06V 10/454 |
| 2022/0287676 | A1 | 9/2022 | Steines et al. |
| 2022/0406061 | A1 | 12/2022 | Quist et al. |
| 2023/0005266 | A1 | 1/2023 | Quist et al. |
| 2023/0029224 | A1 | 1/2023 | Quist et al. |
| 2023/0190136 | A1* | 6/2023 | Kumar ................. A61B 6/5205 |
| | | | 600/587 |
| 2023/0245753 | A1* | 8/2023 | Kumar ................... G16H 40/67 |
| | | | 705/2 |
| 2023/0263573 | A1 | 8/2023 | Bakhishev et al. |
| 2023/0298336 | A1 | 9/2023 | Fathollahi Ghezelghieh et al. |
| 2023/0368398 | A1 | 11/2023 | Figueroa-Alvarez et al. |
| 2023/0386074 | A1 | 11/2023 | Canton et al. |
| 2024/0082019 | A1 | 3/2024 | Jonelagadda |
| 2024/0331737 | A1* | 10/2024 | Leck ...................... G16H 40/63 |
| 2024/0415580 | A1 | 12/2024 | Barban et al. |

FOREIGN PATENT DOCUMENTS

| | | |
|---|---|---|
| JP | 2013509273 | 3/2013 |
| JP | 2013513462 A | 4/2013 |
| JP | 2016506260 A | 3/2016 |
| JP | 2018537155 A | 12/2018 |
| JP | 2019508072 A | 3/2019 |
| KR | 10-1049507 B1 | 7/2011 |
| WO | WO00/64367 A1 | 11/2000 |
| WO | WO2004/095359 A2 | 11/2004 |
| WO | WO2017002388 A1 | 1/2017 |
| WO | WO2019/049503 A1 | 3/2019 |
| WO | WO2019/050612 A1 | 3/2019 |
| WO | WO2019/133071 A1 | 7/2019 |
| WO | WO2020/017212 A1 | 1/2020 |
| WO | WO2020035852 A2 | 2/2020 |
| WO | WO2020/047051 A1 | 3/2020 |
| WO | WO2021/144230 A1 | 7/2021 |

(56) References Cited

FOREIGN PATENT DOCUMENTS

| WO | WO2021/263174 A1 | 12/2021 |
| WO | WO2022/197550 A1 | 9/2022 |
| WO | WO2022/221341 A1 | 10/2022 |
| WO | WO2022/221342 A1 | 10/2022 |
| WO | WO2022/249190 A1 | 12/2022 |

OTHER PUBLICATIONS

Kumar et al.; U.S. Appl. No. 17/996,212 entitled "Systems and methods of computer-assisted landmark or fiducial placement in videos," filed Oct. 13, 2022.

Kumar et al.; U.S. Appl. No. 17/996,217 entitled "Systems and methods for computer-assisted shape measurements in video," filed Oct. 13, 2022.

Jonelagadda et al. U.S. Appl. No. 18/843,235 entitled "Arthroscopic surgery assistance apparatus and method," filed Aug. 30, 2024.

Jonelagadda et al. U.S. Appl. No. 18/864,893 entitled "Surgery evidence report generation," filed Nov. 11, 2024.

Petscharnig et al.; Binary convolutional neural network features off-the-shelf for image to video linking in endoscopic multimedia databases; Multimedia Tools and Applications; 77(21); pp. 28817-28842; Nov. 2018.

Petscharnig; Semi-automatic retrieval of relevant segments from laparoscopic surgery videos; InProceedings of the 2017 ACM on International Conference on Multimedia Retrieval; pp. 484-488; Jun. 6, 2017.

Schoeffmann et al.; Content-based retrieval in videos from laparoscopic surgery; InMedical Imaging 2016: Image-Guided Procedures, Robotic Interventions, and Modeling; SPIE; vol. 9786; pp. 562-571; Mar. 18, 2016.

Wei et al.; Real-time visual servoing for laparoscopic surgery; Controlling robot motion with color image segmentation; IEEE Engineering in Medicine and Biology Magazine: 16(1); pp. 40-45; Jan. 1997.

Stallmo et al.; U.S. Appl. No. 18/878,669 entitled "Surgical analytics and tools," filed Dec. 24, 2024.

Hertel; Trust and Behavioral Intention Toward Generative Adversarial Network (GAN)-Derived Avatar Healthcare Provider (HCP) in Simulated Telehealth Setting. The Florida State University; 2021; retrieved from the internet (https://diginole.lib.fsu.edu/islandora/object/fsu:803248/datastream/PDF/view); on Nov. 3, 2023.

Antico et al.; Deep learning-based femoral cartilage automatic segmentation in ultrasound imaging for guidance in robotic knee arthroscopy; Ultrasound in medicine & biology; 46(2); pp. 422-435; Nov. 22, 2019.

Jonmohamadi et al.; Automatic segmentation of multiple structures in knee arthroscopy using deep learning; IEEE Access; vol. 8; pp. 51853-51861; Mar. 10, 2002.

Jonelagadda et al.; U.S. Appl. No. 18/692,794 entitled "System and method for searching and presenting surgical images," filed Mar. 15, 2024.

Jonelagadda et al.; U.S. Appl. No. 18/693,945 entitled "System and method for computer-assisted surgery," filed Mar. 20, 2024.

Jonelagadda; U.S. Appl. No. 18/637,440 entitled Systems and methods for using image analysis in superior capsule reconstruction,f filed Apr. 16, 2024.

Cheng et al.; Deep learning assisted robotic magnetic anchored and guided endoscope for real-time instrument tracking; IEEE Robotics and Automation Letters, 6(2); pp. 3979-3986; Mar. 17, 2021.

Demirel; A hierarchical task analysis of shoulder arthroscopy for a virtual arthroscopic tear diagnosis and evaluation platform (VATDEP); The International Journal of Medical Robotics and Computer Assisted Surgery; 13(3):e1799;29 pages; (Author Manuscript); Sep. 2017.

Jung et al.; Navigation-assisted anchor insertion in shoulder arthroscopy: a validity study; BMC Musculoskeletal Disorders; 21(1); pp. 1-9; Dec. 2020.

Ruiz U.S. Appl. No. 18/555,248 entitled "Systems and methods for AI-assisted medical image annotation," filed Oct. 12, 2023.

Mourgues et al.; Interactive guidance by image overlay in robot assisted coronary artery bypass. InInternational Conference on Medical Image Computing and Computer-Assisted Intervention; Berlin, Heidelberg: Springer Berlin Heidelberg; pp. 173-181; Nov. 15, 2003.

Winne et al.; Overlay visualization in endoscopic ENT surgery; International journal of computer assisted radiology and surgery; 6(3); pp. 401-406; May 2011.

Jonelagadda et al.; U.S. Appl. No. 19/127,410 entitled "Apparatus and method for interactive three-dimensional surgical guidance," filed May 5, 2025.

Jonelagadda et al.; U.S. Appl. No. 19/101,587 entitled "System and methods for surgical collaboration," filed Feb. 5, 2025.

* cited by examiner frame prediction mask

SYSTEMS AND METHODS FOR AI-ASSISTED SURGERY

CROSS-REFERENCE TO RELATED APPLICATIONS

This PCT application claims priority to Indian Provisional Patent Application No. 20204105990, filed Apr. 13, 2020, and U.S. Provisional Application No. 63,030,695, filed May 27, 2020, and 63,143,367, filed Jan. 29, 2021, the contents of all of which are fully incorporated herein by reference for all purposes.

BACKGROUND

Field of the Invention: Embodiments of the invention relate to systems, devices, and methods to guide diagnostic and surgical procedures, particularly using Artificial Intelligence (AI).

In recent years, Artificial Intelligence has begun to be developed to be used to process images to recognize features of a human face as well as different anatomical structures in a human body. These AI tools can be used to automatically recognize an anatomical feature to assist an operator during a medical procedure. Computational methods such as machine learning and deep learning algorithms can be used for image or language processing to gather and process information generated in a medical procedure. The hope is to use AI algorithms that can then be used to predict or improve the outcome of the surgery or to guide educating new physicians through a virtual or educational procedure. Current AI-assisted surgical systems and methods are still less than ideal in many respects to be used to, for example, guide a surgical procedure. Accordingly, improved AI-assisted surgical systems and methods are desired.

SUMMARY

Various embodiments of the invention provide computer-implemented medical systems, devices, and methods to guide surgery or other medical procedures. Many embodiments do so by identifying and labeling one or more of anatomical features, pathologies and other features in a surgical field of view in real-time, as well as to provide guidance to an operator are described herein. Any mistake made by an operator in the course of a surgery can be costly. For example, it may be difficult or impossible for an operator to know the exact location of a critical anatomical feature that is hidden from a camera (e.g., a camera used during an arthroscopic or endoscopic surgery), or a part of a pathology that was being removed may be missed from the eyes of an operator or a camera view. Therefore, computer-implemented medical systems, devices, and methods such as Artificial Intelligence (AI) tools, particularly for guiding medical procedures can be valuable. These AI tools can have their limitations in accurately and reliably predicting a tool, anatomical structure, or detecting a procedure. In a fast-paced surgical procedure, the AI tool needs to also make predictions with low latency to provide real time assistance to an operator.

Recognized herein is the need for fast, accurate and reliable AI tools to assist an operator in real time during the course of a surgical operation to improve an outcome of the surgery. Accordingly, aspects of the present invention provide a pipeline of machine learning algorithms that is versatile and well trained for unique needs of various medical procedures including various minimally invasive procedures such as arthroscopic, endoscopic, laparoscopic, cardioscopic and related procedures. Examples of such minimally invasive procedures can include one or more of Arthroscopic procedures (e.g., repair of a torn rotator cuff in the shoulder, ACL surgery of the knee, repair of various non-arthritic hip disorders, repair of damaged cartilage in the ankle or removal of bone spurs in the ankle); Gastro-intestinal (GI) procedures (e.g., biopsy of the intestines, removal of polyps, bariatric surgery, stomach stapling/vertical banded gastroplasty), urological procedures (e.g., removal of kidney stone, bladder repair), gynecological procedures (e.g., a dnc, removal of uterine fibroids) and a laparoscopic procedures (e.g., an appendectomy, cholecystectomy, colectomy, hernia repair, nissen fundoplication.

Various embodiments of the invention provide systems, devices, and methods that can receive information (e.g., image(s), voice, user inputs) during a medical procedure (e.g., a surgery), process the received information to identify features associated with the procedure, and provide recommendations based on the identified features. These features may include anatomical parts or devices, or various steps or outcomes of a procedure. Based on identifying the various features in an operation, the systems, devices, and methods described herein can assist a surgeon in the operation by providing recommendations that can include approach angle of a tool, measurement of an anatomical feature or pathology, an action that should be taken or avoided, to name a few.

Aspects of the present invention also aid surgeons (and related medical personnel) intraoperatively by using the images from the surgical field of view and applying Artificial Intelligence (AI) to provide guidance and assistance to the surgeons and other medical staff. We refer to AI modules/algorithms used intraoperatively as Surgical AI.

In a first aspect, the invention provides systems for guiding an arthroscopic procedure. In some embodiments, the systems comprise one or more computer processors and one or more non-transitory computer-readable storage media storing instructions that are operable, when executed by the one or more computer processors, to cause the one or more computer processors to perform operations comprising: receiving at least one image captured by an interventional imaging device; identifying one or more image features in the received at least one image using an image recognition algorithm; labeling the identified one or more image features; and displaying the labeled one or more image features in the at least one image to an operator continuously in the course of the arthroscopic procedure. In some embodiments, the identified one or more image features comprise one or more of an anatomical structure, a surgical tool, a surgical tool element, an operational procedure or an action or a pathology such as torn or injured tissue. Application of embodiments of the system to the guidance of other medical procedures including minimally invasive procedures such as endoscopic, laparoscopic, and interventional cardiovascular procedures is also contemplated.

In various embodiments, the labeled one or more image features may be displayed in real time or concurrent to the arthroscopic procedure. In some embodiments, the arthroscopic procedure is an arthroscopic surgery. In some embodiments, the image recognition algorithm comprises a hierarchical arrangement of processing modules also referred to as software modules or modules.

In some embodiments, the processing modules comprise a plurality of Artificial Intelligence (AI) modules which, in various embodiments, may correspond to a machine learning algorithm, a deep learning algorithm, or a combination of both. In some embodiments, the machine learning algorithm comprises an artificial neural network. Also in various embodiments, the processing modules comprise at least one dataset which may include at least one training dataset.

In various embodiments, the processing modules comprise an upstream module and a downstream module, where the downstream module is more specialized than the upstream module. In some embodiments, the upstream module is configured to identify one or more of an anatomy being operated upon by an operational procedure or an action being performed during the arthroscopic procedure. In some embodiments, the downstream module is configured recognize one or more of an anatomical features of the identified anatomy or a treatment tool feature associated with the operational procedure or the action being performed. In some embodiments, the processing modules comprise a plurality of upstream modules and a plurality of downstream modules. In some embodiments, at least one of the modules of the plurality of upstream modules is configured to select an individual downstream module from the processing modules for use.

In some embodiments, the operational procedure or the action is identified by one or more of the processing modules based at least partially on identification of a surgical tool used during the procedure, for example an arthroscope vs an endoscope. In some embodiments, the interventional imaging device is an arthroscope. In some embodiments, the interventional imaging device is an endoscope. In some embodiments, the image recognition algorithm is configured to identify one or more of a region of operation or an approach portal of entry of an arthroscopic procedure or other medical procedure. In various embodiments, the region of operation may correspond to one or more of a shoulder, a knee or a hip.

In some embodiments, at least one module from the processing modules is selected based at least on identification of one or more of the region of operation (e.g., the shoulder) or the approach portal of entry (e.g., a bursal approach for the shoulder, an anterior approach for the knee). In some embodiments, the operations performed further comprise storing the at least one image in a memory device. In some embodiments, the operations further comprise discarding the at least one image after the displaying the label elements to optimize memory usage.

In various embodiments, the labeled one or more image features further comprises: a pixel-level masked labeling, a bounding box labeling, a frame-level labeling, or a temporal labeling which may configured to be used for various purposes. For example, in some embodiment, the pixel-level masked labeling may be used to display the labeled anatomical structure or the surgical tool. Also in one or more embodiments, the bounding box labeling may be used to display one or more of the labeled pathology, the surgical tool, or a foreign object. Further according to one or more embodiments, the frame-level labeling may be used to display a labeled anatomical region for example that of the shoulder and the temporal labeling may be used to display the labeled operational procedure or action (e.g., a surgical action such as tissue resection, ablation or suturing).

In various embodiments, the operations further comprise providing a suggested action which may be based on a number of factors including results or other output from various modules. For example, in one or more embodiments, the suggested action may be at least partially based on one more of the following: the labeling of the at least one image, results or other output from the upstream or result or other output from the downstream module. Also, in various embodiments the suggested action may have a variety of purposes depending the surgery and situation. For example, the suggested action may be used to assist the operator in the course of the surgery while in other it may for educational or training purposes such as when a surgeon is learning a new procedure and/or during a simulated surgery. In additional embodiments, the suggested action comprises providing a safety warning based at least on identification of a critical anatomical structure (e.g., an artery), a surgical tool, an action, a distance between two or more implants (e.g., if its above or below a critical event) or an adverse event (e.g., bleeding in the surgical field) or biomedical/physiologic data of the patient (e.g., drop in blood pO2, blood pressure, respiration rate, irregular heart rhythm (e.g., arrhythmia or other important physiologic parameter of the patient)

Various embodiments of the invention may also provide suggested surgical actions based one or more of dimensions, positioning and arrangement of structures including anatomical structures and implants within the surgical field. For example, in some surgical situations in which embodiments of the invention are used, the distance between the two or more implants may create a health risk. In particular the actual or allowable distance between two or more positioned implants positioned in the surgical field is different from a predefined distance of the two or more implants making an approach to the surgical field including approaches for position the implants difficult and/or hard to approximate by the human eye particularly when done on screen in two-dimensional view. Accordingly, in these and related embodiments, the suggested action may comprises providing a suggested approach angle which may be suggested a drilling angle for placement of an implant or other surgical action.

Various embodiments of the system may be configured for a number of joint surgeries including for example one or more of shoulder surgery, knee surgery, hip surgery, ankle surgery, hand surgery or elbow surgery. In these and related embodiments one or more of the processing modules described herein may be adapted for each particular site including having data on each particular which may include specialized training data sets.

In some embodiments, the image recognition algorithm is trained using a database. In some embodiments, the database comprises a plurality of training images comprising one or more surgical procedures, surgical tools, surgical tool elements, anatomical structures, or pathologies. In some embodiments, a plurality of augmentation techniques is used to improve the training dataset to improve a robustness of the image recognition algorithm. The surgical images used for such training including augmented training may be selected from a variety of procedures including one or more minimally invasive procedures such as arthroscopic, endoscopic, laparoscopic and cardioscopic procedures which may correspond to one or more of arthroscopic, bariatric, cardiovascular, intestinal, gynecological, urological surgeries or related procedures.

In some embodiments, the augmentation techniques comprise rotating the training images to improve the robustness against a position or an orientation of a patient during the arthroscopic procedure. In some embodiments, the augmentation techniques comprise flipping the training images along a vertical axis to improve the robustness against procedures performed on a right or a left side of a patient. In some embodiments, the augmentation techniques comprise enlarging or cropping the training images to improve the robustness against changes in a depth of view.

In some embodiments, the at least one image is generated from a surgical video stream. In some embodiments, the surgical video stream is an arthroscopic surgery video stream. In various embodiments, the surgical video stream may be monocular or stereoscopic. In these and related embodiments, embodiment of the system may be adapted to receive and recognize each type of view (monocular and stereoscopic) and switch back and forth between appropriate processing methods when the views are switch.

Another aspect of the present invention provides computer-implemented methods for guiding an arthroscopic procedure. In some embodiments, the methods comprise: receiving at least one image captured by an interventional imaging device; identifying one or more image features in the received at least one image using an image recognition algorithm; labeling the identified one or more image features; and displaying the labeled one or more image features in the at least one image to an operator continuously in the course of the arthroscopic procedure. In some embodiments, the identified one or more image features comprising one or more of an anatomical structure, a surgical tool, a surgical tool element, an operational procedure or action, or a pathology. In some embodiments, the labeled one or more image features are displayed in real time or concurrent to the arthroscopic procedure.

In some embodiments, the arthroscopic procedure is an arthroscopic surgery. In some embodiments, the image recognition algorithm comprises a hierarchical arrangement of processing modules. In some embodiments, the processing modules comprise a plurality of Artificial Intelligence (AI) modules. In some embodiments, the processing modules comprise at least a machine learning algorithm, a deep learning algorithm, or a combination of both. In some embodiments, the machine learning algorithm comprises an artificial neural network.

In some embodiments, the processing modules comprise at least one dataset which may include at least one training dataset. In some embodiments, the processing modules comprise an upstream module and a downstream module, where the downstream module being more specialized than the upstream module. In some embodiments, the upstream module is configured to identify one or more of an anatomy being operated upon by an operational procedure or an action being performed during the arthroscopic procedure. In some embodiments, the downstream module is configured to one or more of recognize an anatomical feature of the identified anatomy or recognize a treatment tool feature associated with the operational procedure or the action being performed. In some embodiments, the processing modules comprise a plurality of upstream modules or a plurality of downstream modules. In some embodiments, the at least one of the modules of the plurality of upstream modules is configured to select an individual downstream module from the processing modules for use. In some embodiments, the operational procedure or the action is identified partially based on the identifying the surgical tool.

In some embodiments, the interventional imaging device is an arthroscope. In some embodiments, the interventional imaging device is an endoscope. In some embodiments, the image recognition algorithm is configured to identify one or more of a region of operation or an approach portal of entry of the arthroscopic procedure. In some embodiments, the region of operation is a shoulder. In some embodiments, the region of operation is a knee. In some embodiments, at least one module from the processing modules is selected based at least on the identifying the one or more of the region of operation or the approach portal of entry.

In some embodiments, the operations performed further comprise storing the at least one image in a memory device.

In some embodiments, the operations further comprise discarding the at least one image after the displaying the label elements to optimize memory usage.

In some embodiments, the labeled one or more image features further comprises: a pixel-level masked labeling, a bounding box labeling, a frame-level labeling, or a temporal labeling. In some embodiments, the pixel-level masked labeling is used to display the labeled anatomical structure or the surgical tool. In some embodiments, the bounding box labeling is used to display the labeled pathology, the surgical tool, or a foreign object. In some embodiments, the frame-level labeling is used to display a labeled anatomical region. In some embodiments, the temporal labeling is used to display the labeling the operational procedure or the action.

In some embodiments, the operations further comprise providing a suggested action. In some embodiments, the suggested action is at least partially based on the labeling of the at least one image. In some embodiments, the suggested action is at least partially based on the upstream module. In some embodiments, the suggested action is at least partially based on the downstream module. In some embodiments, the suggested action is to assist the operator in the course of the surgery. In some embodiments, the suggested action is provided for educational purposes. In some embodiments, the suggested action comprises providing a safety warning based at least on identification of a critical anatomical structure, or a distance of two or more implants.

In some embodiments, the distance of the two or more implants creates a health risk. In some embodiments, the distance of the two or more implants is different from a predefined distance of the two or more implants. In some embodiments, the suggested action comprises providing a suggested approach angle. In some embodiments, the suggested approach angle may comprise a drilling angle.

In some embodiments, the method is configured for a shoulder surgery. In some embodiments, the method is configured for a knee surgery. In some embodiments, the image recognition algorithm is trained using a database. In some embodiments, the database comprises a plurality of training images comprising one or more surgical procedures, surgical tools, surgical tool elements, anatomical structures, or pathologies.

In some embodiments, a plurality of augmentation techniques is used to improve the training dataset to improve a robustness of the image recognition algorithm. In some embodiments, the augmentation techniques comprise rotating the training images to improve the robustness against a position or an orientation of a patient during the arthroscopic procedure. In some embodiments, the augmentation techniques comprise flipping the training images along a vertical axis to improve the robustness against procedures performed on a right or a left side of a patient. In some embodiments, the augmentation techniques comprise enlarging or cropping the training images to improve the robustness against changes in a depth of view.

In some embodiments, the at least one image is generated from a surgical video stream. In some embodiments, the surgical video stream is an arthroscopic surgery video stream. In some embodiments, the surgical video stream is monocular. In some embodiments, the surgical video stream is stereoscopic.

Another aspect of the present invention provides a method of training an algorithm for guiding an arthroscopic procedure. In some embodiments, the method comprises: receiving a set of image features based on one or more images relating to the arthroscopic procedure; receiving a training dataset; recognizing one or more of the image features in images of the training dataset; and building an image recognition algorithm based at least partially on the recognition of the one or more image features and the received training dataset. In some embodiments, the training dataset comprises one or more labeled images relating to the arthroscopic procedure. In some embodiments, the training dataset comprises one or more labeled images relating to the arthroscopic procedure one or more image features relate to visual properties of one or more of an anatomical structure, a surgical tool, a surgical tool element, an operational procedure or action, or a pathology. In some embodiments, the image recognition algorithm is configured to identify and label the one or more image features in an unlabeled image relating to the arthroscopic procedure.

In some embodiments, the labeled one or more image features are displayed in real time or concurrent to the arthroscopic procedure. In some embodiments, the image recognition algorithm comprises a hierarchical arrangement of processing modules. In some embodiments, the processing modules comprise a plurality of individual image processing modules. In some embodiments, the plurality of individual image processing modules comprises a first module for identifying the arthroscopic procedure in place, a second module for recognizing and labeling one or more surgical tools and surgical tool elements, a third module for recognizing and labeling one or more anatomical structures, or a combination thereof.

In some embodiments, the processing modules comprise a plurality of Artificial Intelligence (AI) modules. In some embodiments, the processing modules comprise at least a machine learning algorithm, a deep learning algorithm, or a combination of both. In some embodiments, the machine learning algorithm comprises an artificial neural network.

In some embodiments, the processing modules comprise at least one dataset. In some embodiments, the processing modules comprise at least one training dataset.

In some embodiments, the processing modules comprise an upstream module and a downstream module, where the downstream module being more specialized than the upstream module. In some embodiments, the upstream module is configured to identify one or more of an anatomy being operated upon by an operational procedure or an action being performed during the arthroscopic procedure. In some embodiments, the downstream module is configured to one or more of recognize an anatomical feature of the identified anatomy or recognize a treatment tool feature associated with the operational procedure or the action being performed. In some embodiments, the processing modules comprise a plurality of upstream modules or a plurality of downstream modules. In some embodiments, at least one of the modules of the plurality of upstream modules is configured to select an individual downstream module from the processing modules for use.

In some embodiments, identifying one or more image features in the at least one image further comprises selecting one or more processing modules from a plurality of processing modules, where the selection is at least partially based on the region and/or the portal of the arthroscopic surgery. In some embodiments, the operational procedure or the action is identified partially based on the identifying the surgical tool. In some embodiments, the unlabeled image is captured by an interventional imaging device. In some embodiments, the interventional imaging device is an endoscope. In some embodiments, the unlabeled image is generated from a surgical video stream.

In some embodiments, the surgical video stream is an arthroscopic surgery video stream. where the endoscopic surgery is an arthroscopic surgery. In some embodiments, the surgical video stream is monocular. In some embodiments, the surgical video stream is stereoscopic.

In some embodiments, the image recognition algorithm is configured to identify one or more of a region of operation or an approach portal of entry of the arthroscopic procedure. In some embodiments, the region of operation is a shoulder. In some embodiments, the region of operation is a knee. In some embodiments, at least one module from the processing modules is selected based at least on the identifying the one or more of the region of operation or the approach portal of entry.

In some embodiments, the image recognition algorithm stores the labeled image in a memory device. In some embodiments, the image recognition algorithm discards the labeled image to minimize memory usage.

In some embodiments, the labeled image comprises: a pixel-level masked labeling, a bounding box labeling, a frame-level labeling, or a temporal labeling. In some embodiments, the pixel-level masked labeling is used to display the labeled anatomical structure or the surgical tool. In some embodiments, the bounding box labeling is used to display the labeled pathology, the surgical tool, or a foreign object. In some embodiments, the frame-level labeling is used to display a labeled anatomical region. In some embodiments, the temporal labeling is used to display the labeling the operational procedure or action.

In some embodiments, the training dataset is configured for a shoulder surgery. In some embodiments, the image recognition algorithm is trained for a shoulder surgery using the training dataset configured for a shoulder surgery. In some embodiments, the training dataset is configured for a knee surgery. In some embodiments, the image recognition algorithm is trained for a knee surgery using the training dataset configured for a knee surgery. In some embodiments, the training dataset comprises a plurality of training images comprising one or more surgical procedures, surgical tools, surgical tool elements, anatomical structures, or pathologies.

In some embodiments, a plurality of augmentation techniques is used to improve the training dataset to improve a robustness of the image recognition algorithm. In some embodiments, the augmentation techniques comprise rotating the training images to improve the robustness against a position or an orientation of a patient during the arthroscopic procedure. In some embodiments, the augmentation techniques comprise flipping the training images along a vertical axis to improve the robustness against procedures performed on a right or a left side of a patient. In some embodiments, the augmentation techniques comprise enlarging or cropping the training images to improve the robustness against changes in a depth of view.

Another aspect of the present invention provides a method for implementing a hierarchical pipeline for guiding an arthroscopic surgery. In some embodiments, the system comprises one or more computer processors and one or more non-transitory computer-readable storage media storing instructions that are operable, when executed by the one or more computer processors, to cause the one or more computer processors to perform operations comprising: (a) receiving at least one image captured by an interventional imaging device; (b) identify one or more image features of a region of treatment or a portal of entry in the region based on at least one upstream module; (c) activating a first downstream module to identify one or more image features of an anatomical structure, or a pathology based at least partially on the identified one or more image features in step (b); (d) activating a second downstream module to identify one or more image features of a surgical tool, a surgical tool element, an operational procedure or action relating to the arthroscopic surgery based at least partially on the identified one or more image features in step (b); (e) labeling the identified one or more image features; and (f) displaying the labeled one or more image features in the at least one image continuously to an operator in the course of the arthroscopic surgery.

In some embodiments, the at least one upstream module comprises a first trained image processing algorithm. In some embodiments, the at least one upstream module comprises a first trained image processing algorithm first downstream module comprises a second trained image processing algorithm. In some embodiments, the at least one upstream module comprises a first trained image processing algorithm first downstream module comprises a second trained image processing algorithm second downstream module comprises a third trained image processing algorithm. In some embodiments, the steps (c) and (d) are independent from one another. In some embodiments, the first, second, or third trained image processing algorithms comprise at least a machine learning algorithm, a deep learning algorithm, or a combination of both. In one or more embodiments, the machine learning algorithm includes an artificial neural network.

In some embodiments, the machine learning or the deep learning algorithms are trained using at least one training dataset. In some embodiments, the training dataset is configured for a shoulder surgery. In some embodiments, the training dataset is configured for a knee surgery. In some embodiments, the training dataset comprises a plurality of training images comprising one or more surgical procedures, surgical tools, surgical tool elements, anatomical structures, or pathologies.

In some embodiments, a plurality of augmentation techniques is used to improve the training dataset to improve a robustness of the image recognition algorithm. In some embodiments, the augmentation techniques comprise rotating the training images to improve the robustness against a position or an orientation of a patient during the arthroscopic procedure. In some embodiments, the augmentation techniques comprise flipping the training images along a vertical axis to improve the robustness against procedures performed on a right or a left side of a patient. In some embodiments, the augmentation techniques comprise enlarging or cropping the training images to improve the robustness against changes in a depth of view.

In some embodiments, the first, second, or third trained image processing algorithms store the displayed images with labeled features in a memory device. In some embodiments, the first, second, or third trained image processing algorithms discard the displayed images with labeled features to minimize memory usage.

In some embodiments, the arthroscopic procedure is an arthroscopic surgery. In some embodiments, the at least one image is generated from a surgical video stream. In some embodiments, the surgical video stream is an endoscopic surgery video stream. In some embodiments, the surgical video stream is monocular. In some embodiments, the surgical video stream is stereoscopic.

Another aspect of the present invention provides a non-transitory computer readable medium comprising machine executable code that, upon execution by one or more computer processors, implements any of the methods above or elsewhere herein.

Another aspect of the present invention provides a system comprising one or more computer processors and computer memory coupled thereto. The computer memory comprises machine executable code that, upon execution by the one or more computer processors, implements any of the methods above or elsewhere herein.

Embodiments of the systems and methods of the invention are particularly useful in aiding the surgeon during surgery such as arthroscopic surgier by providing real time display of anatomical structures, pathologies, pathology repair and selected measurements within the surgical field. Such display reduces errors due to misidentified tissue structures and measurements in turn leading to improved surgical and patient outcomes. It also does so by reducing the cognitive load on the surgeon allowing them to focus on the procedure and at the time alerting them to potentially adverse actions, conditions or results during the course of the surgery that they may otherwise miss due to focus or hyper focus on critical tasks. Such alerts prevent or reduce potential adverse events during surgery by alerting the surgeon before they happen and/or contemporaneously to their occurrence to allow the surgeon to take appropriate action for their prevention or mitigation. In use such alerts lead to both reduced morbidity and mortality as well as improved acute surgical outcomes and long-term outcomes for the patient as the surgery is performed with no or fewer errors and with more precision and accuracy in the surgical actions performed (e.g., accuracy of implant placement or removal of damaged or diseased, tissue while preserving healthy tissue).

Additional aspects and advantages of the present invention will become readily apparent to those skilled in this art from the following detailed description, wherein only illustrative embodiments of the present invention are shown and described. As will be realized, the present invention is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the present invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
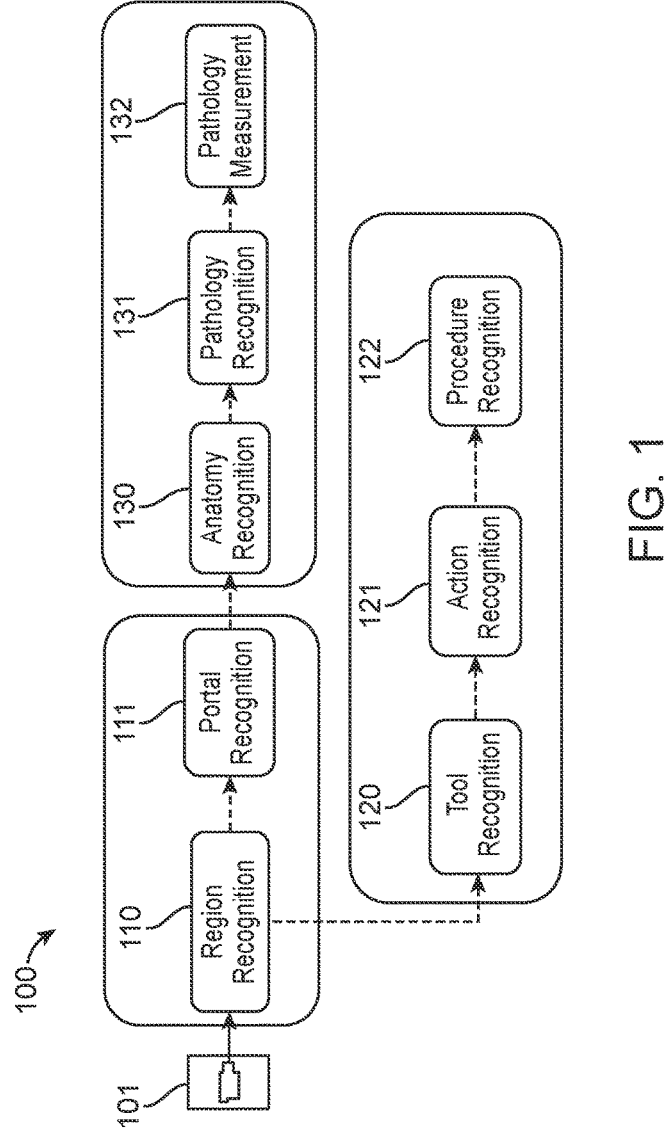
FIG. 1 shows a flow chart of an example of hierarchical arrangement of modules in a system for AI-assisted surgery, according to some embodiments.

While various embodiments of the present invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed as is explained in more detail below.

Various embodiments of the invention provide icomputer-implemented medical systems, devices, and methods for assisting surgeons in an intraoperative setting using AI. The systems, devices, and methods disclosed herein may improve upon existing methods of surgical assistance by providing an improved classification (e.g., real-time) of various elements involved in a surgical operation (e.g., surgical tools, anatomical features, anatomical pathology/ injury features, operation procedures). One or more embodiments of the systems, devices, and methods provided herein may achieve this objective through the use AI methods (e.g., machine learning, deep learning) to build a classifier which improves a real-time classification of elements involved in a surgical operation. Various embodiment of AI approaches and implementation described herein may leverage large datasets in order gain new insights from the datasets. The classifier model may improve real-time characterization of various elements involved in an operation which may lead to higher operation success rate for example due to fewer errors due to misidentified anatomical structures. The classifier model may provide an operator (e.g., surgeon, operating room nurse, surgical technician) with information for making more accurate and timely decisions (e.g., labeling critical anatomical features in real-time). This leads to fewer errors and more the performance of more accurate and precise surgical actions such as the placement of an implant (e.g., an anchor) at desired location or more complete removal of damaged or diseased tissue while preserving healthy tissue (e.g., such as a frayed tendon or cartilage or tumorous tissue) from a particular anatomical structure(s) at the surgical site.

The computer-implemented medical systems, devices, and methods as disclosed herein may improve upon existing methods of clinical decision support systems by leveraging parameters related to various elements in the context of a surgical operation to generate accurate real-time decisions continuously. A surgical operation involves various elements such as the patient's body with various parts and anatomical complexity, plurality of tools and devices, actions based on the surgical procedure as well as actions based on a non-routine event that may occur in the surgery. The systems, devices, and methods disclosed herein can operate continuously with the changing environment of the surgical operation to make classifications and suggestions based on a plurality of AI modules organized to make decisions in a hierarchical manner. For example, the classifier described herein can classify anatomical features (e.g., shoulder, knee, organ, tissue, or pathology) while a view of the endoscopic camera may change during the operation. Similarly, the systems, devices, and method described here can recognize surgical tools as they appear in the field of view.

The systems, devices, and methods as disclosed herein may be used to classify various elements involved in an operation. For example, the classifier disclosed herein can identify and label anatomical structures (e.g., anatomical parts, organs, tissues), surgical tools, or a procedure being performed in an operation.

The invention may help with recognizing critical structures (e.g., nerves, arteries, veins, bone, cartilage, ligaments) or pathologies (e.g., a tissue that needs to be removed). The critical structures may be visible or hidden in the field of view. The systems, devices, and methods described herein can identify and mark the critical structures (e.g., color markings on the video stream). Systems according to many embodiments may comprise a plurality of surgical AI modules organized to make decisions in a hierarchical manner. The surgical AI assist modules disclosed herein may analyze video feeds of the surgical field of view and render decisions in a substantially continuous manner. These modules can be connected by a messaging framework which can process the flow of video data, and a plurality of outputs (e.g., decisions). The AI systems may react to changes in the surgical field of view. The methods and systems of the disclosed invention may be applied to various surgical operations including different anatomical regions and organs. The surgical AI assist can work when surgeons change views, i.e., access the surgical field from different approach portals.

Reference will now be made in detail to various embodiments, examples of which are illustrated in the accompanying drawings. In the following detailed description, numerous specific details are set forth in order to provide a thorough understanding of the present invention and the described embodiments. However, the embodiments of the present invention are optionally practiced without these specific details. In other instances, well-known methods, procedures, components, and circuits have not been described in detail so as not to unnecessarily obscure aspects of the embodiments. In the drawings, like reference numbers designate like or similar steps or components.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, the terms "comprises," "comprising," or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "subject" and "patient" are used interchangeably. As used herein, the terms "subject" and "subjects" refers to a human being. In certain embodiments, the subject is going through a surgical operation. In certain embodiments, the subject is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "surgical AI" or "surgical AI module", as used herein, generally refer to a system, device, or method that uses Artificial Intelligence algorithms to assist before, during, and/or after a surgical operation. A surgical AI module can be defined as a combination of input data, machine learning or deep learning algorithms, training datasets, or other datasets.

The term "machine learning", as used herein, may generally refer to computer algorithms that can improve automatically over time. Any description herein of machine learning can be applied to Artificial Intelligence, and vice versa, or any combination thereof.

As used herein, the terms "continuous," "continuously" or any other variation thereof, generally refer to a substantially uninterrupted process or a process with time delay that is acceptable in the context of the process.

The terms "video stream" or "video feed", as used herein, refer to data generated by a digital camera. Video feed may be a sequence of static or moving pictures.

The terms "region," "organ," "tissue," "structure", as used herein, may generally refer to anatomical features of the human body. A region may be larger than an organ and may comprise an organ. An organ may comprise one or more tissue types and structures. A Tissue may refer to a group of cells structurally joined to complete a common function. A structure can refer to a part of a tissue. In some embodiments, a structure may refer to one or more parts of one or more tissues joined together to create an anatomical feature.

The terms "surgical field of view," or "field of view," as used herein, refer to the extent of visibility captured by an interventional imaging device. Field of view may refer to the extent of visual data captured by a digital camera that is observable by human eye.

The term "decision," as described herein, may refer to outputs from a machine learning or AI algorithm. A decision may comprise labeling, classification, prediction, etc.

The term "interventional imaging device," as used herein, generally refers to an imaging device used for medical purposes. The interventional imaging device may refer to an imaging device that is used in a surgical operation. The surgical operation, in some embodiments, may be a simulation of an operation.

The term "operator," used herein, refers to a medical professional involved in a surgical operation. An operator can be a surgeon, an operating room nurse, a surgical technician.

One aspect of the invention provides a system for guiding an arthroscopic procedure. The system may comprise one or more computer processors and one or more non-transitory computer-readable storage media storing instructions that are operable, when executed by the one or more computer processors, to cause the one or more computer processors to perform operations comprising: receiving at least one image captured by an interventional imaging device; identifying one or more image features in the received at least one image using an image recognition algorithm; labeling the identified one or more image features, wherein the identified one or more image features comprising one or more of an anatomical structure, a surgical tool, a surgical tool element, an operational procedure or an action, or a pathology; and displaying the labeled one or more image features in the at least one image to an operator continuously in the course of the arthroscopic procedure. For example, in some embodiments, the operational procedure or the action may be identified partially based on identifying the surgical tool. In some embodiments, an interventional imaging device is an endoscope. In some embodiments, an interventional imaging device is an arthroscope. The operations may further comprise storing the image in a memory device. In some embodiments, the operations further comprise discarding the image after displaying the labeled image features, to optimize a memory usage.

In some embodiments, the arthroscopic procedure may be an arthroscopic surgery (or arthroscopy). An arthroscopic surgery, also known as arthroscopy or keyhole surgery can be a minimally invasive surgical procedure (e.g., it requires only a small incision) on a joint. The arthroscopy may comprise either a diagnostic or therapeutic procedure. Therapeutic aspects or types of arthroscopy may also comprise surgical repairs, such as, for example, debridement, or cleaning, of a joint to remove bits of torn cartilage, ligament reconstruction, or synovectomy (removal of the joint lining) The arthroscopy can be performed using an arthroscope. The arthroscope may be inserted into a subject's body to perform the arthroscopic procedure in or around the joint through a small incision. The arthroscope may be an endoscope. The arthroscope may comprise a fiberoptic scope. The arthroscope may be flexible or rigid. The arthroscope may comprise a camera (e.g., a digital camera), a light source, a lens to create the image of the field of view, or a mechanism to carry the image to a sensor. The sensor may comprise a global shutter (e.g., a CCD sensor) or a rolling shutter (e.g., a CMOS sensor). The images captured by the arthroscope may be displayed on a display (e.g., a monitor). An operator (e.g., a surgeon) may use the displayed images (e.g., video feed from the arthroscope) to perform the surgery.

Arthroscopic surgeries may use small incisions through which tools and endoscopes may access a joint to diagnose or repair a pathology. Due to the minimally invasive nature of the procedure, patients may experience less pain, heal faster than conventional surgeries or experience less bleeding. However, arthroscopic surgeries can be more technically demanding than conventional surgeries (e.g., an open surgery). In arthroscopy, an operator (e.g., a surgeon) may operate with limited field of view, using small tools and with a restricted range of movement. Since the field of view may restricted, the surgeon may, for example, have to pan the scope to cover a target anatomy. Nonlimiting example of challenges associated with an arthroscopy may comprise tracking a target location, such as, for example, an intended repair location, a recognition of a pathology (e.g., cancerous tissue), critical structures (e.g., nerves, arteries, veins, bone, cartilage, ligaments), etc.; visual orientation with respect to an anatomical structure; intraoperatively measuring of a dimension (e.g., sizing a rotator cuff tear); keeping track of bones or tissue boundaries for placing an implant when using a graft; a field of view that may not be sufficient for an operator to place an anchor in a predefined location, where the procedure may require a larger field of view; or correlating preoperative diagnostic imaging with intraoperative field of view to, for example recognize a critical sight. The critical sight may comprise a pathology (e.g., a tumor or a cyst), or a predefined implant or repair site. In some embodiments, the systems and methods provided herein may be configured for a shoulder surgery. In some embodiments, the systems and methods provided herein may be configured for a knee surgery.

In some embodiments, an image captured by imaging device (e.g., an arthroscope) may be received by a computer system. The computer system may comprise an image recognition or algorithm or another related algorithm. The image recognition algorithm may identify one or more features in the image received from the arthroscope. The image recognition algorithm may be configured to identify one or more of a region of operation or an approach portal of entry (or a portal) of the arthroscopic procedure (e.g., an arthroscopic surgery). In some embodiments, the region of operation is a shoulder. In some embodiments, the region of operation is a knee.

The image recognition algorithm may comprise a processing module. The image recognition algorithm may comprise an arrangement of processing modules. The arrangement of processing modules may be hierarchical. For example, a hierarchical arrangement of processing modules may comprise a first processing module that may be upstream of a second processing module and/or downstream of a third processing module. The image recognition algorithm may comprise at least two processing modules an upstream module and a downstream module. In some embodiments, the downstream module may be more specialized (e.g., configured to identify features associated with a particular anatomical structure, pathology, tissue type, procedure, etc.) than the upstream module. In some embodiments, a module may be a generic module. A specialized module may comprise a portal recognition module, an anatomy recognition module, modules associated with specific anatomical structures (e.g., a shoulder module, a knee module), a pathology recognition module, modules associated with a specific pathology (e.g., cancer, defects in the cartilages, rotator cuff tears, dislocated/torn labrum, torn ACL, anterior cruciate ligament, torn meniscus, torn bicep tendon, inflamed synovial tissue, or femoral acetabular impingement (FAI)) or a pathology measurement module. A generic module may comprise a tool recognition module, an action recognition module (e.g., drilling, grinding, cleaning, etc.). In some embodiments, the processing module may comprise a plurality of upstream modules, a plurality of downstream modules, or a combination of both. In some embodiments, at least one of the plurality of upstream modules may be configured to select at least one downstream module from the plurality of downstream modules of the processing modules to further process an image. In some embodiments, identifying one or more features identified in the image may further comprise selecting one or more processing modules from the plurality of AI modules, wherein the selection is at least partially based on an output from at least one upstream module. In some embodiments, a processing module is selected based at least on the identifying the one or more of the region of operation or the approach portal of entry (or portal).

In some embodiments, an upstream module may be configured to identify one or more of an anatomy being operated upon by an operational procedure or an action being performed during the arthroscopic procedure. In some embodiments, a downstream module may be configured to recognize one or more of an anatomical feature of the identified anatomy associated with the operational procedure or the action being performed. In some embodiments, a downstream module may be configured to recognize a treatment tool feature associated with the operational procedure or the action being performed.

The processing modules may comprise an Artificial Intelligence (AI) module. In some embodiments, the processing modules may comprise a plurality of AI modules. In some embodiments, the processing modules or the plurality of AI modules may comprise at least a machine learning algorithm, a deep learning algorithm, or a combination of both. The machine learning algorithm may comprise a trained machine learning algorithm. The machine learning algorithm may comprise an artificial neural network. In some embodiments, the processing modules or an AI in the processing modules may comprise at least one dataset. In some embodiments, the processing modules or an AI in the processing modules may comprise at least a training dataset.

FIG. 1 is a flow chart that shows an example of a hierarchical arrangement 100 of modules. In some embodiments, a first module may comprise a region recognition module 110 to determine a field of surgery. A region recognition module may receive an image 101 (e.g., a frame from a video feed) from an imaging device (e.g., an arthroscope). In some embodiments, the region recognition module 110 may not recognize a field of surgery in the image. The region recognition module 110 may then stop transfer of the image to other modules and/or discard the frame. In some embodiments, the region recognition module 110 may recognize a field of surgery in the image. The region recognition module 110 may then send the image to other modules downstream of the region recognition module 110 comprising a generic module, a specialized module, or both. For example, modules downstream of region recognition module 110 may comprise a portal recognition module 111, a tool recognition module 120, or both. The image may be sent to two or more modules substantially simultaneously (e.g., in parallel). The image may be sent to two or more modules consecutively (e.g., in series). The image may be sent to a tool recognition module 120, an action recognition module 121, or a procedure recognition module 122 in order mentioned herein. In some embodiments, the tool recognition module 120 may recognize a tool in the image. Subsequently, the module 121 may determine an action based at least in part on the recognized tool. The module 121 may then send the image to a procedure recognition module, which then determines a surgical procedure being performed based at least in part on the determined action and/or the recognized tool. The region recognition module 110 may also send the image to the portal recognition module 111 in parallel to the tool recognition module 120. The portal recognition module 111 may then determine a portal of entry associated with the region recognized by region recognition module 110. Based at least in part on the portal of entry recognized by portal recognition module 111, an image may be sent to one or more specialized modules which form a specialized or customized pipeline. Such a specialized pipeline may be specialized to a particular anatomical region or site, (e.g., the shoulder, knee or hip) and may comprise specialized modules (e.g., AI trained for a specific anatomical structure or pathology). One or more modules in the specialized pipeline may be activated upon recognition of region of entry (e.g., a bursal region) by the portal recognition module 111.

In some embodiments, labeling an image feature further comprises: a pixel-level masked labeling, a bounding box labeling, a frame-level labeling, or a temporal labeling. In some embodiments, the pixel-level masked labeling is used to display the labeled anatomical structure or the surgical tool. In some embodiments, the bounding box labeling is used to display the labeled pathology, the surgical tool, or a foreign object. In some embodiments, the frame-level labeling is used to display a labeled anatomical region. In some embodiments, temporal labeling is used to display the labeling of the operational procedure or the recognized action.

Figure 7A:
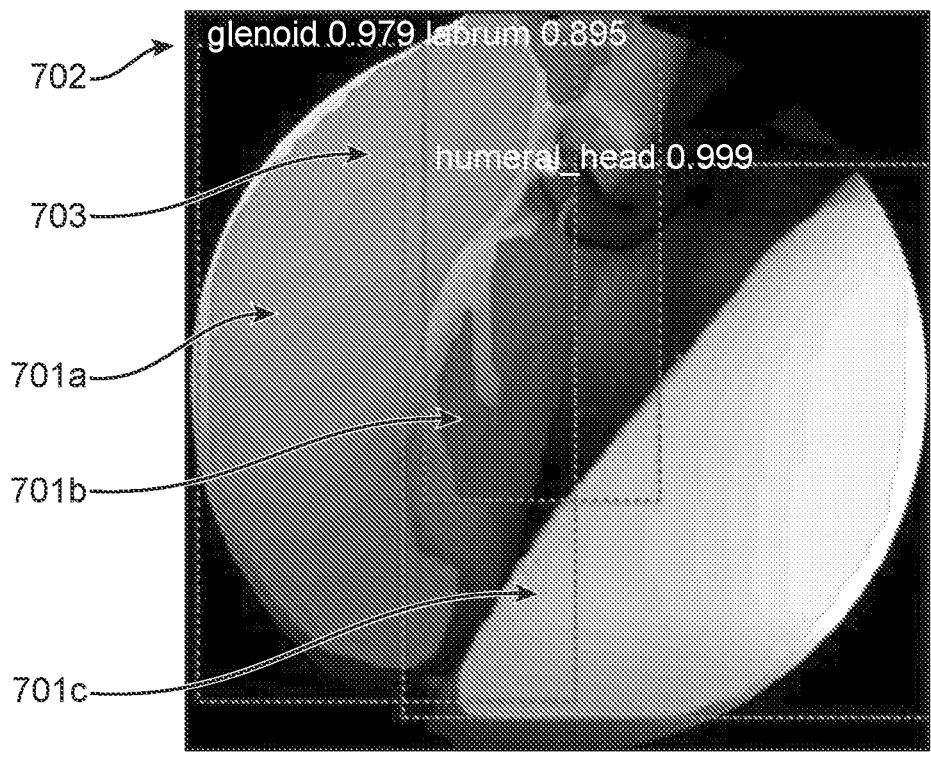
FIG. 7A shows an example of recognizing and labeling anatomical structures, according to some embodiments.
Figure 7B:
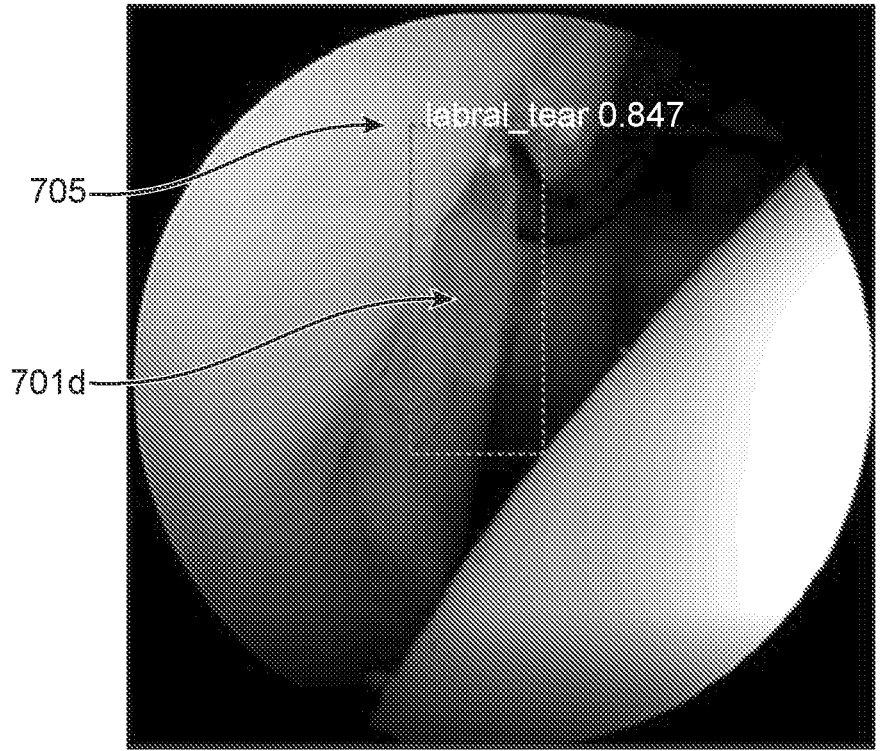
FIG. 7B shows an example of recognizing and labeling a pathology, according to some embodiments.

Downstream of region recognition module 110 and portal recognition module 111, one or more images may be sent to one or more modules to recognize and/or label one or more features on the image(s). Examples of labeled images are shown in FIGS. 7A-7B. An anatomy recognition module 130 shown in FIG. 1 may receive one or more images from the region recognition module 110 and portal recognition module 111 and may recognize and label anatomical structures (as shown in FIG. 7A). Different color masks 701a, 701b, 701c, 701d, along with descriptive labels 702, 703 may be used to differentiate the recognized anatomical structures. Downstream of the anatomy recognition module 130, a pathology recognition module 131 shown in FIG. 1 may receive the image from the anatomy recognition module 131 and may recognize and label one or more pathologies on the recognized anatomical structure (as shown in FIG. 7A). As described above in various embodiment, region recognition module 130, anatomy recognition module and any subsequent recognition or measurement module are specialized to a particular anatomical site (e.g., the shoulder or knee) be virtue of information identified or otherwise obtained by portal recognition module 111 or a similar module. Because of this specialization, less memory, programming and processing capability/r are required of a computer system performing analysis and processing of images received from an imaging device used during the surgery. These reduced performance requirements (e.g., reduced memory, processing power) allows for various image processing functions such as one or more of anatomical, pathology recognition and associated be done by device in or near operating room (aka an edge device), rather than having to be done remotely e.g. via the Cloud which further speeds up the process and makes it more reliable since no data need be sent up and back over the Internet to the Cloud or an external computer device. Moreover, in various embodiments no Internet or other network connection is required at all. In this way, one or more of the reliability, speed and cybersecurity of embodiments of the invention are substantially improved.

FIG. 7B shows an example of a pathology which has been identified and labeled using a colored mask 701d as well as a descriptive label 705. For example, a tear has been detected and labeled in the labrum (FIG. 7B). Downstream of the pathology recognition module 131, a pathology measurement module 132 shown in FIG. 1 may receive the image from the pathology recognition module 131 and may provide one or more measurements for the pathology identified and labeled.

Figures 2A, 2B:
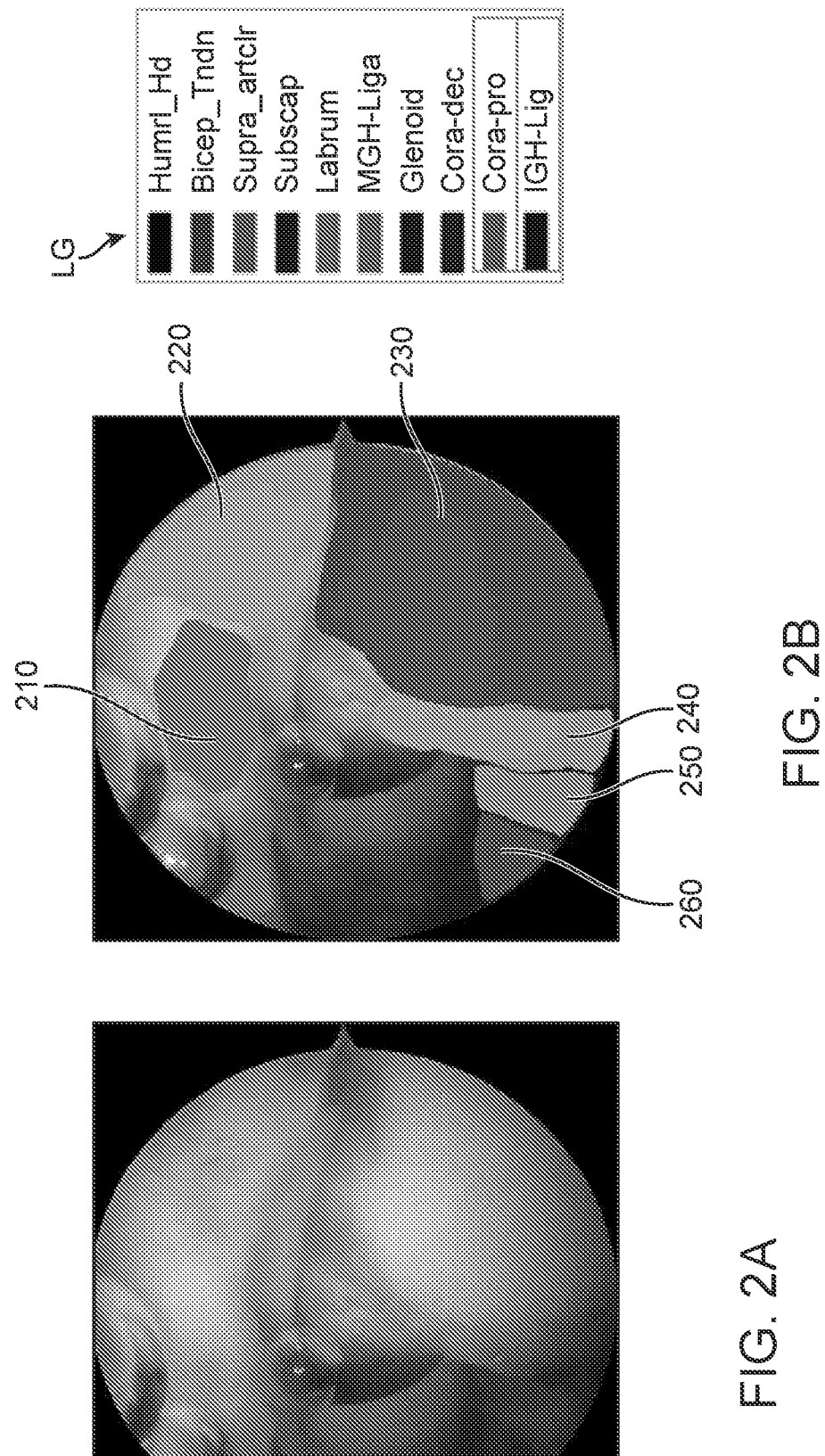
FIG. 2A shows an image of an arthroscopic surgical procedure, according to some embodiments.
FIG. 2B shows an example of labeling features in an arthroscopic surgical procedure, according to some embodiments.

FIG. 2A shows an image of an arthroscopic surgical procedure. The image was then provided as an input to the system described herein. The image was processed using an image recognition model configured to analyze shoulder surgery images. The image recognition model may comprise specialized modules. For example, the specialized module may be used to analyze intraarticular region (FIG. 2A-2B). FIG. 2B shows an example of labeling features in the image provided in FIG. 2A using the methods and systems described herein. Features 210 (bicep tendon (Bicep_Tndn)), 220 (Labrum), 230 (Glenoid), 240 (coracoid process (Cora-pro)), 250 (middle glenohumeral ligament (MGH-Liga)), and 260 (subscapularis (Subscap)) may be provided labels, such as with color masks and a legend LG (which also can provide color or pattern guide for other anatomical features that may be labeled and/or masked, such as the humeral head (Humrl_Hd), supra articular process (Supra_artclr), descending portion of coracoid (Cora-dec), inner glenohumeral ligament (IGH-Liga), to name a few) as shown in FIG. 2B.

Figures 8A, 8B, 8C, 8D, 8E, 8F, 8G, 8H, 8I, 8J, 8K, 8L, 8M, 8N, 8O, 8P, 8Q, 8R, 8S, 8T, 8U, 8V:
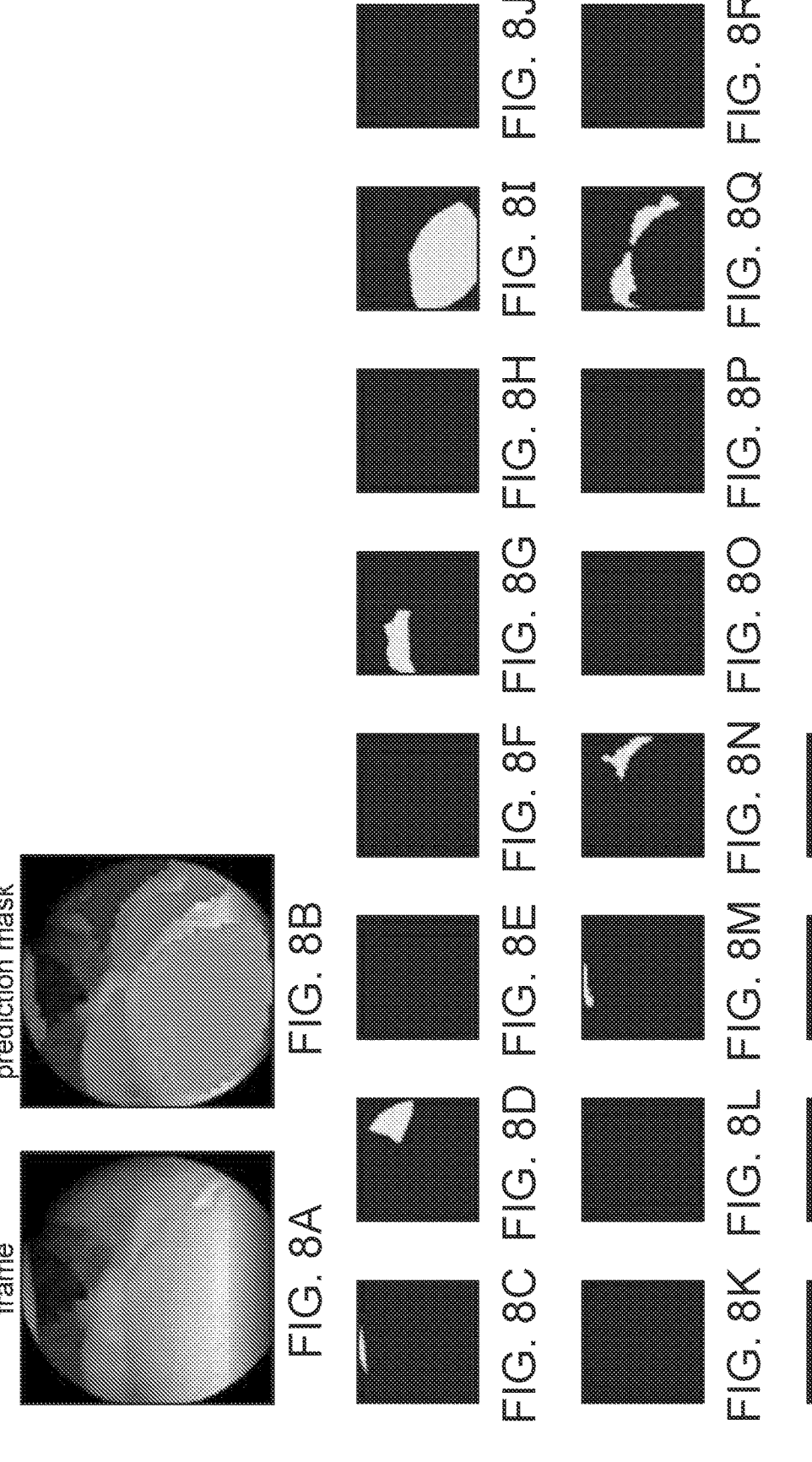
FIG. 8A shows an example of an image of an arthroscopic surgical procedure, according to some embodiments.
FIG. 8B shows an example of an image of an arthroscopic surgical procedure labeled using image recognition algorithms, according to some embodiments.
FIGS. 8C-8L show examples of anatomical structures in an image labeled by subject matter experts, according to some embodiments.
FIGS. 8M-8V show examples of anatomical structures in an image labeled by AI algorithms, according to some embodiments.

FIG. 8A-8V show examples of identifying various features in a surgical procedure using the systems and methods described herein. An image from the surgical field of view (e.g., a frame of a video stream) may be provided (FIG. 8A). The image recognition model may produce predictions for different classes of anatomical structures (e.g., humeral head, glenoid, subscapularis, bicep tendon, ligaments, tendons, etc.) that can be recognized in the input image (FIGS. 8M (humeral head), 8N (bicep tendon), 8O (supra articular surface), 8P (subscapularis), 8Q (labrum), 8R (middle glenohumeral ligament), 8S (glenoid), 8T (descending portion of coracoid), 8U (coracoid process), 8V (inner glenohumeral ligament)). The predictions made by the recognition model were compared to a series of labels generated for the same classes of anatomical structures made by subject matter experts (FIGS. 8C (humeral head), 8D (bicep tendon), 8E (supra articular surface), 8F (subscapularis), 8G (labrum), 8H (middle glenohumeral ligament), 8I (glenoid), 8J (descending portion of coracoid), 8K (coracoid process), 8L (inner glenohumeral ligament)). After predicting distinct classes of anatomical structures, the predictions are combined into an output image provided with a prediction mask (FIG. 8B). The output image may contain different color masks to differentiate different classes of anatomical structures identified. The classification process described herein may be applied to consecutive frames received from a video camera. The labeled output image may then be overlaid on the video stream. The overlay may be performed in real-time or in substantially close to real-time.

Figure 3A:
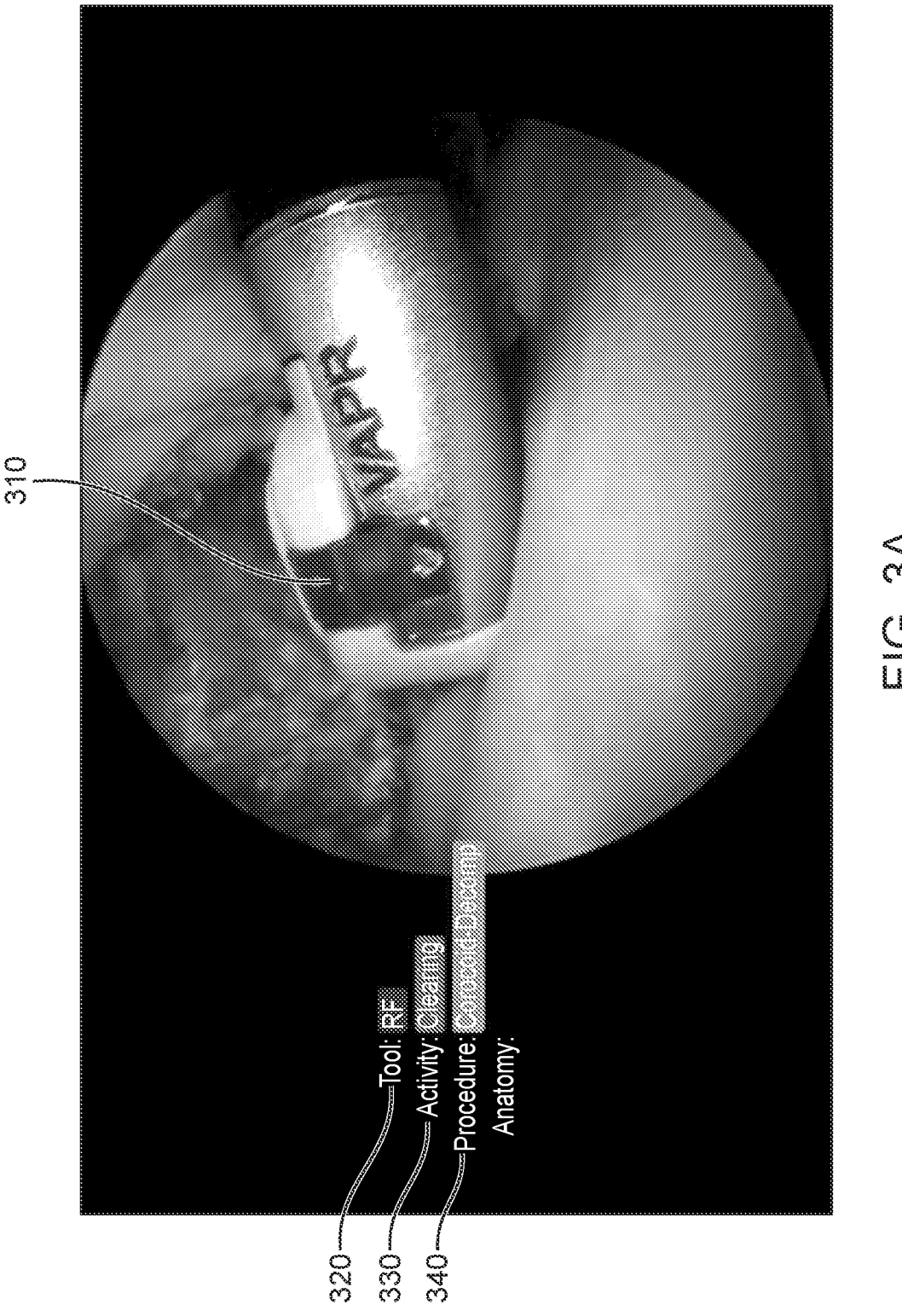
FIG. 3A shows an example of labeling a tool, an action, or a procedure in an image captured by an arthroscope, according to some embodiments.

FIG. 3A shows an example of labeling a tool, an action, or a procedure in an image captured by an arthroscope. The image recognition algorithm recognized and labeled a tool 310 (e.g., a radiofrequency ablation tool). Based on the recognized tool 310, a tool identify label 320 may be provided for the type of tool identified (e.g., a radiofrequency ablation tool), an action recognition module may identify the action being performed was and provide an activity label 330 (e.g., showing a cleaning being performed). A procedure recognition module may determine the procedure performed and provide a procedural label 340, for example showing a coronoid decompression procedure being performed.

Figure 3B:
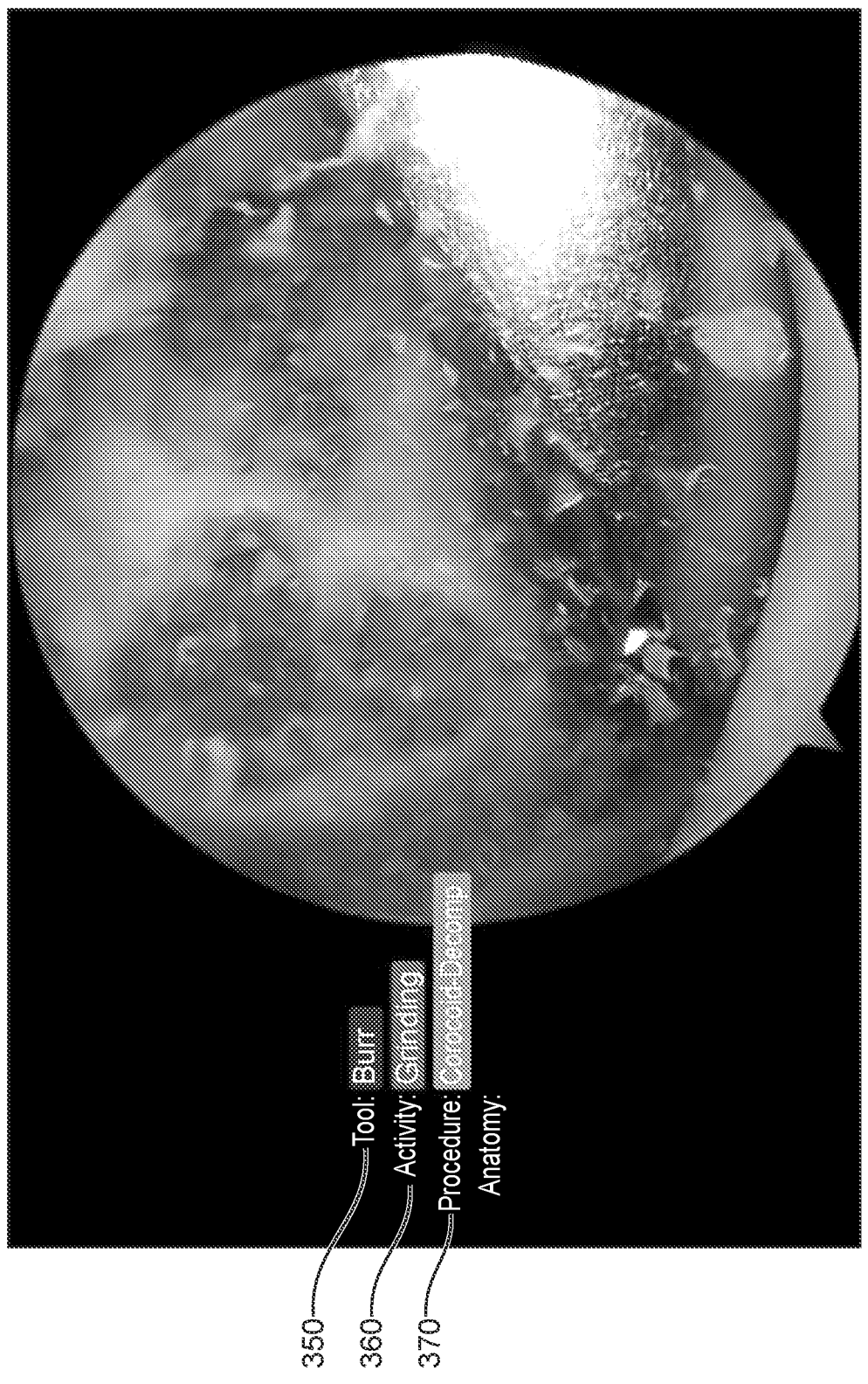
FIG. 3B shows another example of labeling a tool, an action, or a procedure in an image captured by an arthroscope, according to some embodiments.
Figure 3C:
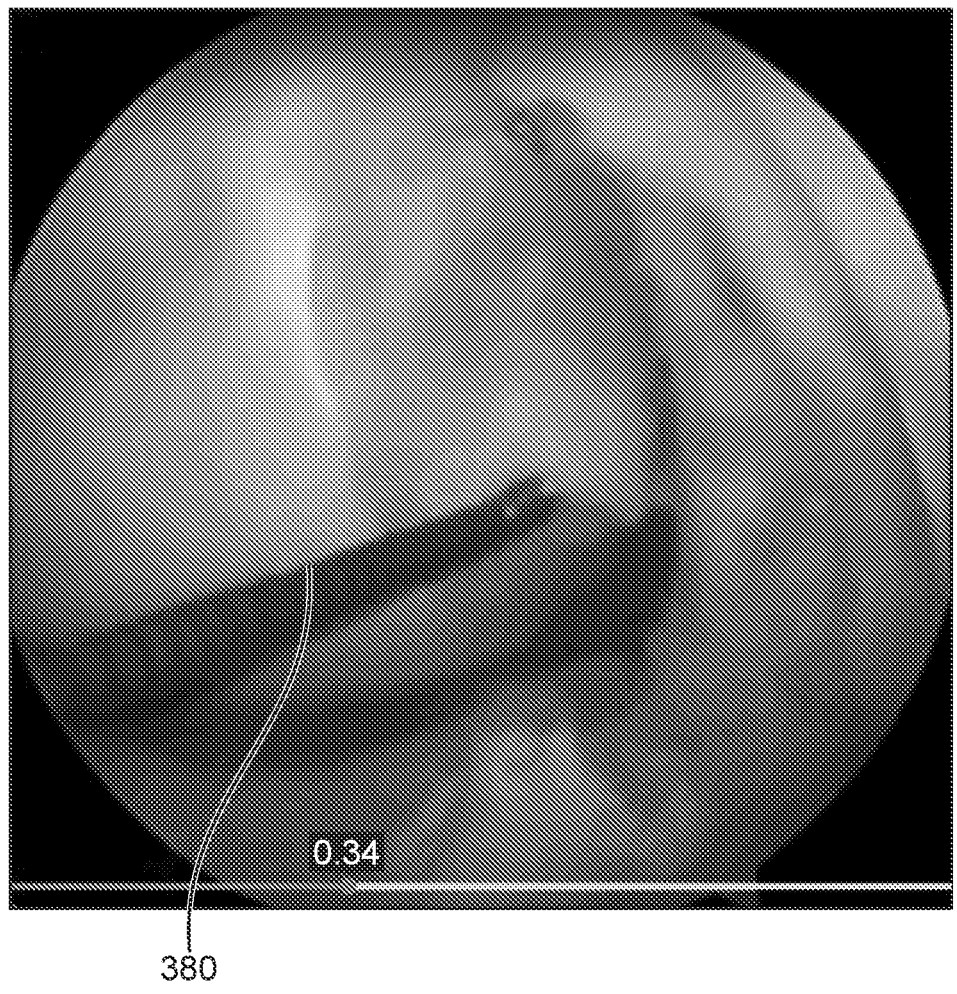
FIG. 3C shows an example of recognizing an arbitrary tool in a field of surgery, according to some embodiments.

FIG. 3B shows another example of labeling a tool, an action, or a procedure in an image captured by an arthroscope. The image recognition algorithm recognized and labeled an arthroscopic burrs tool at label 350. A tool may comprise a surgical probe, a shaver, a burr grinder, a drill tool, an implant, a drill guides, a radio frequency or other ablation tool, an anchor, a graspers, suture passers, or a scissors. Based on the recognized tool, grinding was determined to be the action being performed at a label 360 using an action recognition module. A procedure recognition module determined the procedure to be a coronoid decompression procedure at a label 370. An arthroscopic surgery may comprise actions being performed on areas comprising a shoulder, a knee or a hip. A shoulder surgery may be performed in an intraarticular region and/or the bursal region. Anatomical structures that may be recognized in the intraarticular region may comprise humeral head, labrum, glenoid, supraspinatus, bicep tendon, glenoid humeral ligaments, subscapularis. Anatomical structures that may be recognized in the bursal region may comprise acromian, clavicle, humeral head, bursal, or rotator cuff. A surgical procedure may be initiated from one or more portals of entry into the region of operation (e.g., intraarticular region, bursal region, a portal of entry adjacent to a knee). A view of the surgical field of view may therefore vary based at least on the portal or an angle of entry used in an operation. FIG. 3C shows an example of recognizing an arbitrary tool 380 in a field of surgery.

In some embodiments, the operations further comprise providing a suggested action to an operator (e.g., a surgeon). The operator may be performing the procedure (e.g., arthroscopic surgery). The operator may be a person other than the surgeon. The operator may operate the imaging device (e.g., an arthroscope). In some embodiments, the suggested action is to assist an operator in the course of the surgery (e.g., an arthroscope). For example, a surgeon may require a measurement of a tissue or pathology, and the methods and systems described herein may provide the measurement to the surgeon intraoperatively. In some embodiments, the suggested action may comprise a safety warning to allow the operator to know of a potential safety issue. For example, the system may recognize a distance of one or more implants being implanted in a patient to be different from a predefined safe distance. The distance may be a distance between two or more implants from one another. In some embodiments, the distance may be a distance of one or more implants from an anatomical structure, an anatomical feature, or a pathology. A suggested action may comprise avoiding a critical anatomical feature such as, for example, a vein, an artery, nerves, bone, cartilage, or ligaments. In some embodiments, the suggested action comprising a safety warning is based at least on an identified anatomical feature, a recognized tool, an identified action or a combination thereof. For example, a tool may be recognized (e.g., a burr grinder) that may potentially damage a tissue (e.g., a cartilage). When the system recognizes a tool, for example, a burr grinder in close proximity of a tissue recognized, for example, as cartilage, the system may generate a safety warning A suggested action may comprise suggesting an approach angle for a device. The approach angle may be an approach angle of a drilling tool. In some embodiments, the suggested action is provided for educational purposes. For example, a video stream of a medical procedure (e.g., arthroscopy) can be used for educational purposes. The methods and systems described herein may be used to label features overlaid on the video stream (e.g., images or frames of the video stream). The suggested actions may also be overlaid on the video stream for educational purposes.

In some embodiments, the suggested action is at least partially based on the labeling (e.g., labeling of the features) of the image. The suggested action may be at least in part based on an output from one of the plurality of modules (e.g., upstream modules, or downstream modules). In some embodiments, the suggested action is at least partially based on the output from at least one of the modules of the plurality of upstream modules. In some embodiments, the suggested action is at least partially based on the output from at least one of the modules of the plurality of downstream modules.

In some embodiments, the image may be generated from a surgical video stream. In some embodiments, the surgical video stream is an arthroscopic surgery video stream. In some embodiments, the surgical video stream is monocular or stereoscopic. In some embodiments, the labeling of features on an image may be performed at a speed similar to a rate of acquiring images from an imaging device. The arthroscope may generate consecutive images (e.g., a video feed) at a rate of at least about 10 frames per second (fps).

In some embodiments, the image recognition algorithm is trained using a database (e.g., a training dataset). In some embodiments, the database may comprise a plurality of training images. The plurality of training images may comprise one or more surgical procedures, surgical tools, surgical tool elements, anatomical structures, or pathologies. In some embodiments, a training dataset may be generated using an image editing technique. An image editing technique may comprise augmenting an image of a region, a portal, an anatomical structure or an anatomical feature with an image of a surgical tool. The augmented image may then be used to train the image recognition algorithm to recognize the tool within a context of the region, the portal, the anatomical structure or the anatomical feature. In some embodiments, the image editing, or augmentation techniques may comprise rotating a training image to improve a robustness of the image recognition algorithm against a position or an orientation of a patient, for example, during the arthroscopic surgery. In some embodiments, the image editing, or augmentation techniques may comprise enlarging or cropping the training images to improve the robustness against changes in a depth of view. In some embodiments, the image editing, or augmentation techniques may comprise flipping a training image along a vertical axis to improve the robustness against procedures performed on a right or a left side of a patient. The surgical images used for such training including image editing and augmented training may be selected from a variety of procedures including one or more minimally invasive procedures such as arthroscopic, endoscopic, laparoscopic and cardioscopic procedures which may correspond to one or more of arthroscopic, bariatric, cardiovascular, intestinal, gynecological, urological surgeries or related procedures.

Figure 4:
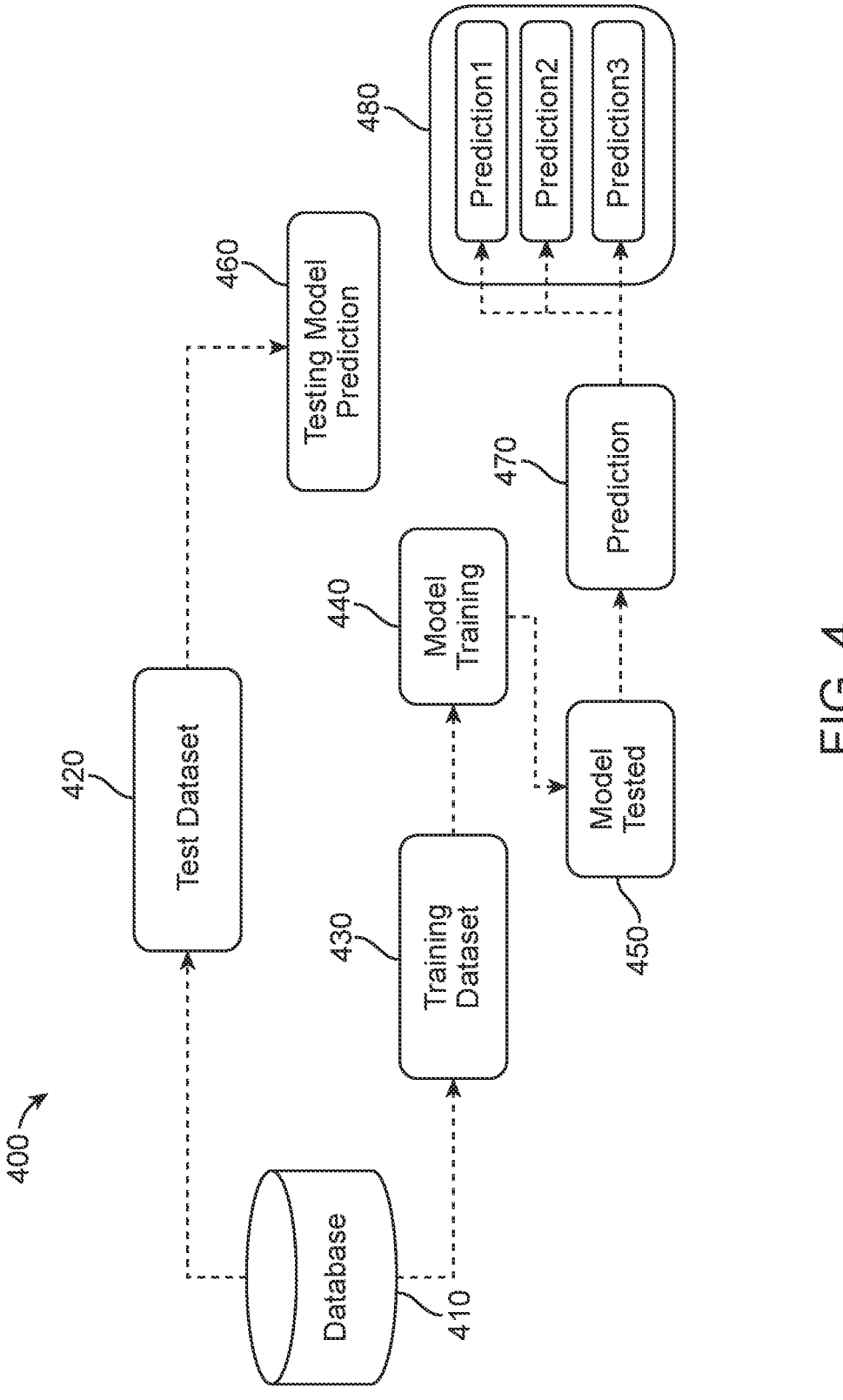
FIG. 4 shows a flowchart of an example of training an image recognition algorithm, according to some embodiments.

FIG. 4 is a flowchart of an example of training an image recognition algorithm. An AI training method 400 may comprise a dataset 410. The dataset 410 may comprise images of a surgical tool, an anatomical structure, an anatomical feature, a surgical tool element, an image acquired from a video feed of an arthroscope, a portal of a surgery, a region of a surgery, etc. The dataset may further comprise an imaged that has been edited or augmented using the methods described hereinbefore. The images in the dataset 410 may be separated into at least a test dataset 420 and a training dataset 430. The dataset 410 may be divided into a plurality of test datasets and/or a plurality of training datasets. At a model training step 440, a training dataset may be used to train an image recognition algorithm. For example, a plurality of labeled images may be provided to the image recognition algorithm to train an image recognition algorithm comprising a supervised learning algorithm (e.g., a supervised machine learning algorithm, or a supervised deep learning algorithm). Unlabeled images may be used to build and train an image recognition algorithm comprising an unsupervised learning algorithm (e.g., an unsupervised machine learning algorithm, or an unsupervised deep learning algorithm). A trained model may be tested using a test dataset (or a validation dataset). A test dataset may comprise unlabeled images (e.g., labeled images where a label is removed for testing a trained model). The trained image recognition algorithm may be applied to the test dataset and the predictions may be compared with actual labels associated with the data (e.g., images) that were removed to generate the test dataset in a testing model predictions step 460. A model training step 440 and a testing model predictions step 460 may be repeated with different training datasets and/or test datasets until a predefined outcome is met. The predefined outcome may be an error rate. The error rate may be defined as one more of an accuracy, a specificity, or a sensitivity or a combination thereof. The tested model 450 may then be used to make a prediction 470 for labeling features in an image from an imaging device (e.g., an arthroscope) being used in the course of a medical procedure (e.g., arthroscopy). The prediction may comprise a plurality of predictions 480 comprising a region of a surgery, a portal of the surgery, an anatomy, a pathology, a tool, an action being performed, a procedure being performed, etc.

Figure 6:
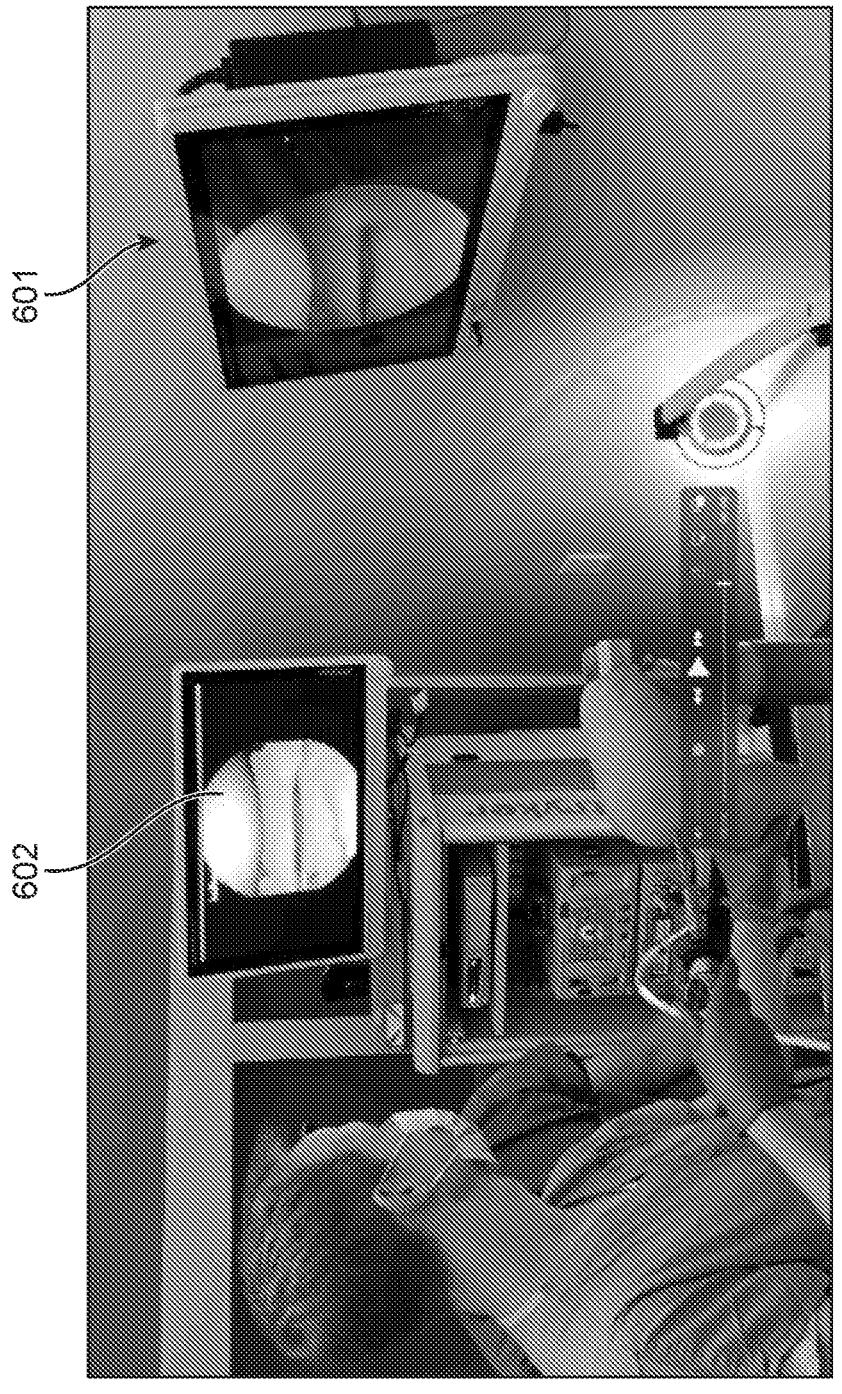
FIG. 6 shows an example of an AI pipeline used in a simulated knee surgery, according to some embodiments.

An example of an AI pipeline, as described herein, used in a simulated knee surgery as described herein is provided in FIG. 6. In this ad related examples, a video feed of the surgery may be provided on a first screen 601. A second screen may provide an AI inference of the surgical field 602 comprising anatomical masks as described hereinbefore. The AI feed may be overlaid on the video feed of the surgery in real-time. The AI feed and the video feed of the surgery may be provided on one screen simultaneously.

Another aspect of the invention provides a computer-implemented method for guiding an arthroscopic procedure. In some embodiments, the computer-implemented method may comprise receiving at least one image captured by an interventional imaging device; identifying one or more image features in the received at least one image using an image recognition algorithm; labeling the identified one or more image features, wherein the identified one or more image features; and displaying the labeled one or more image features in the at least one image to an operator continuously in the course of the arthroscopic procedure. The labeled one or more image features may be displayed in real time or concurrent to the arthroscopic procedure. The identified one or more image features may comprise one or more of an anatomical structure, a surgical tool, a surgical tool element, an operational procedure or action, or a pathology.

Another aspect of the invention provides a method of training an algorithm for guiding an arthroscopic procedure. The method of training an algorithm may comprise receiving a set of image features based on one or more images relating to the arthroscopic procedure; receiving a training dataset, wherein the training dataset comprises one or more labeled images relating to the arthroscopic procedure; recognizing one or more of the image features in images of the training dataset; building an image recognition algorithm based at least partially on the recognition of the one or more image features and the received training dataset. The one or more image features may relate to relate to visual properties of one or more of an anatomical structure, a surgical tool, a surgical tool element, an operational procedure or action, or a pathology. The image recognition algorithm may be configured to identify and label the one or more image features in an unlabeled image relating to the arthroscopic procedure.

The image recognition algorithm may be trained using training data. Training data may comprise images, where subject matter experts trace outlines of various anatomical structures, pathologies, tools, etc. The process of training is similar to the example shown in FIG. 8A-8V, as described elsewhere herein. These subject matter experts labeled images may be also used to train the algorithm to, for example, recognize a given tool performing a given action. A combination of tool recognition, anatomical recognition, and an action recognition may be used to predict a surgical procedure being performed. For example, first an anatomical feature or region (e.g., bursa) may be recognized, which may then trigger other recognition modules to recognize a tool or an action being performed. FIG. 3B shows an example, where a region of operation is recognized as being bursa, then a burr tool identified with label 350 and a grinding action identified with label 360 may be recognized. The combination of these predictions may lead to recognizing the procedure as the coracoid decompression identified with label 370.

Figure 9:
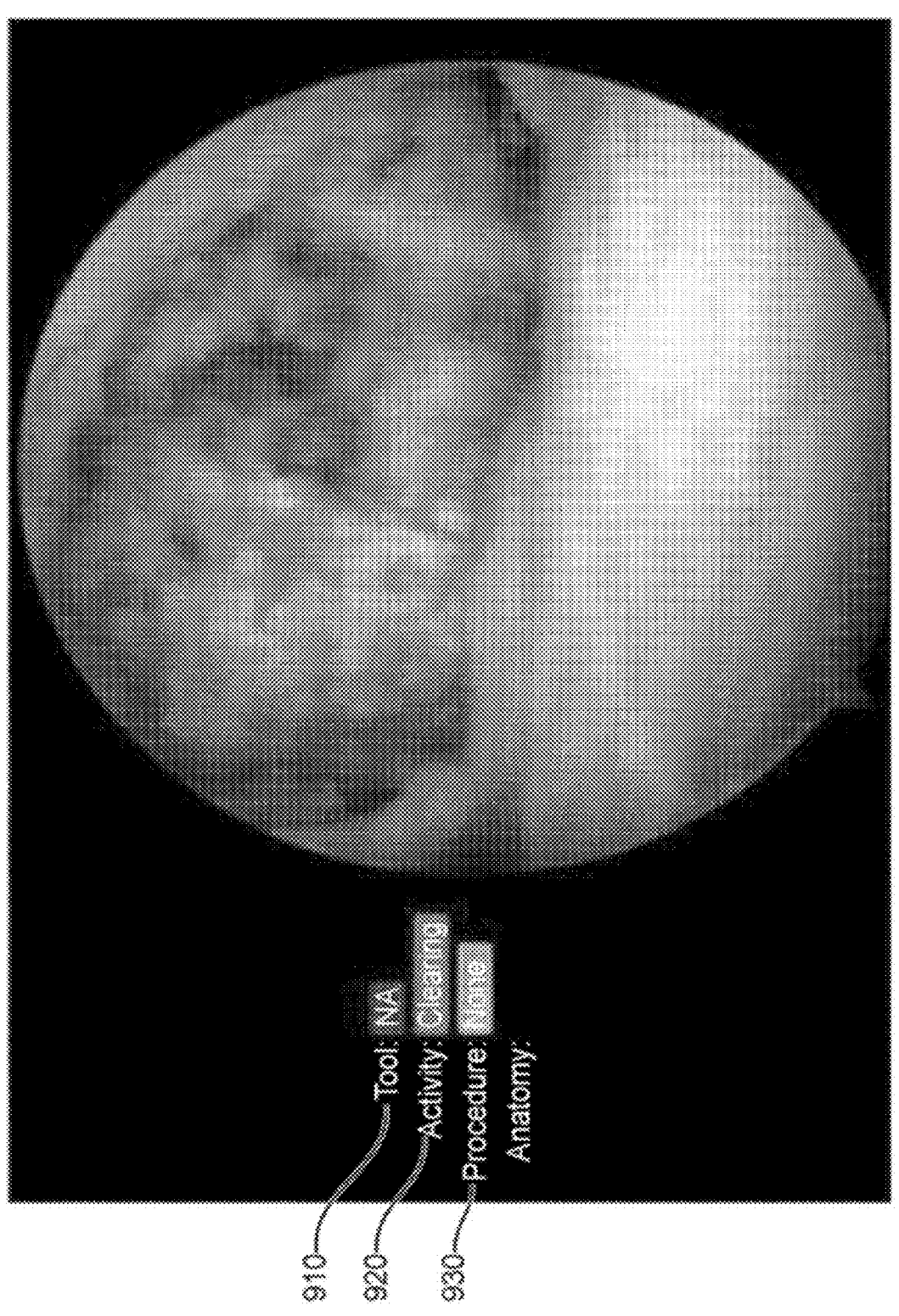
FIG. 9 shows an example of an action recognized by the system for AI-assisted surgery, according to some embodiments.

In some embodiments, a tool may not be present in the image. The system may still recognize an activity at least partially based on anatomical features being recognized, a previous image analyzed, or a combination thereof. The previous image processed by the system may have comprised recognizing a tool, an action, a surgical procedure, or combinations thereof. FIG. 9 shows an example of an action (e.g., clearing) identified with a label 920 being recognized by the system, while a tool is not present in the image as shown by a label 910 (showing NA or non-applicability). A surgical procedure identified with a label 930 may not be assigned to an image (FIG. 9). For example, the operator may swap tools during the course of a surgical procedure. In some embodiments, the swapping of the tools may take several seconds or minutes. The system and method described herein, can retain a memory of the recognized tool. In some other cases, the tool may be obscured or not recognizable (e.g., by movement of camera, orientation of the tool may render the tool unrecognizable). To compensate for the short term loss of tool recognition, an AI architecture may be used. The AI architecture may comprise a neural network architecture. The neural network architecture may comprise a long short term memory (LSTM).

Figure 10:
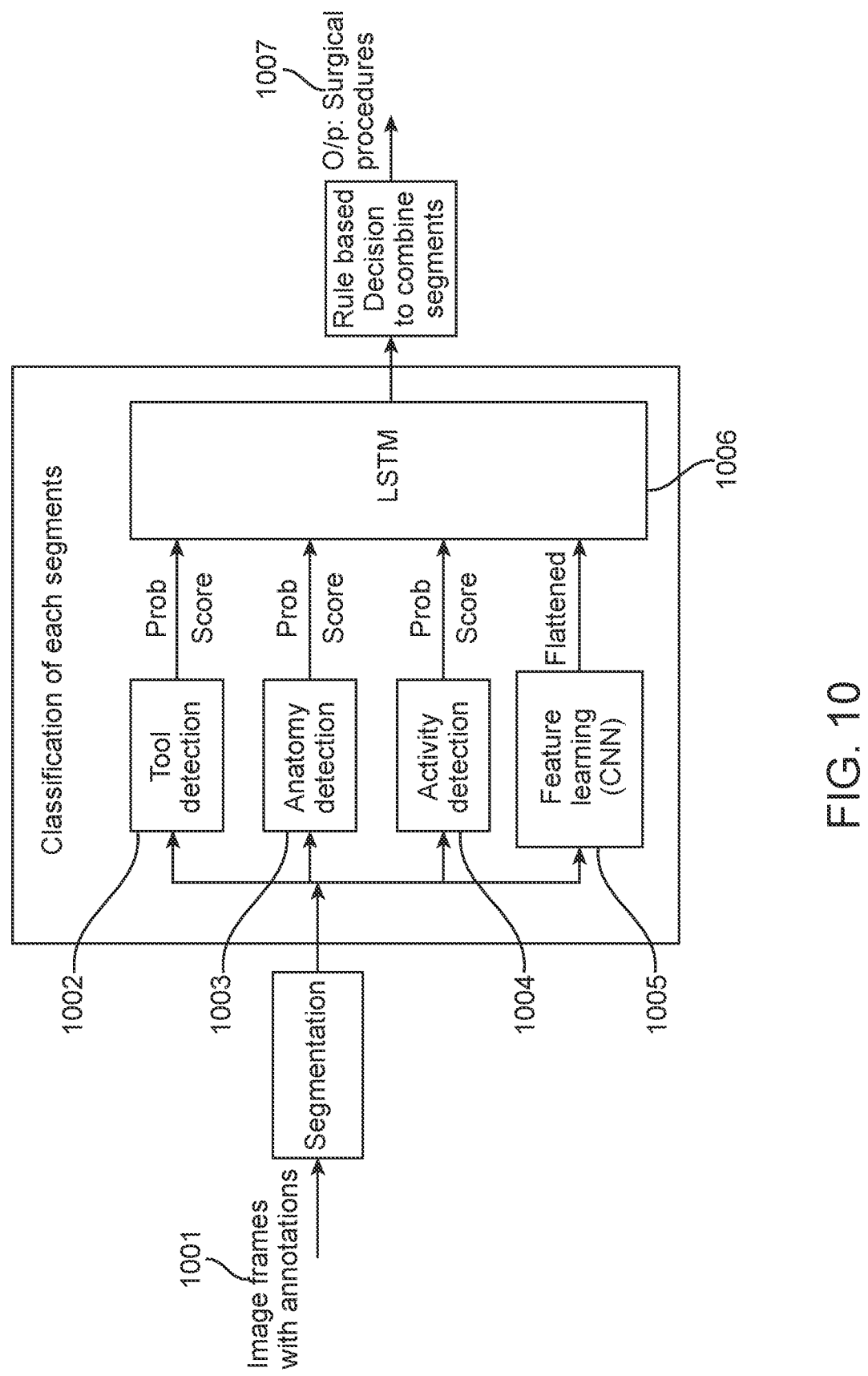
FIG. 10 shows an example flowchart of the process of identifying a surgical procedure, according to some embodiments.

FIG. 10 shows an example flowchart of the process of identifying a surgical procedure, as described herein. Image frames with annotations 1001 may be received and segmented into one or more segments using one or more classifier models. The classifier models may comprise a tool recognition model 1002, an anatomy detection model 1003, an activity detection model 1004, or a feature learning model 1005. The outputs from the one or more classifiers may be combined using a long short term memory (LSTM) 1006. LSTM is an artificial recurrent neural network (RNN) classifier that may be used to predict based on image recognition at one moment compared to what has been recognized prior. In other words, LSTM may be used to generate a memory of a context of the images being processed, as described herein. The context of the images is then used to predict a stage of the surgery comprising a surgical procedure. A rule-based decision to combine the classified segments into one image may then be processed to identify/predict a surgical procedure 1007 being performed.

Another aspect of the invention provides a system for implementing a hierarchical pipeline for guiding an arthroscopic surgery. The system may comprise one or more computer processors and one or more non-transitory computer-readable storage media storing instructions that are operable, when executed by the one or more computer processors, to cause the one or more computer processors to perform operations. The operations may comprise (a) receiving at least one image captured by an interventional imaging device; (b) identify one or more image features of a region of treatment or a portal of entry in the region based on at least one upstream module; (c)) activating a first downstream module to identify one or more image features of an anatomical structure, or a pathology based at least partially on the identified one or more image features in step (b); (d) activating a second downstream module to identify one or more image features of a surgical tool, a surgical tool element, an operational procedure or action relating to the arthroscopic surgery based at least partially on the identified one or more image features in step (b); (e) labeling the identified one or more image features; and displaying the labeled one or more image features in the at least one image continuously to an operator in the course of the arthroscopic surgery. The at least one upstream module may comprise a first trained image processing algorithm. The downstream module may comprise a second trained image processing algorithm. The second downstream module may comprise a third trained image processing algorithm.

Figure 11A:
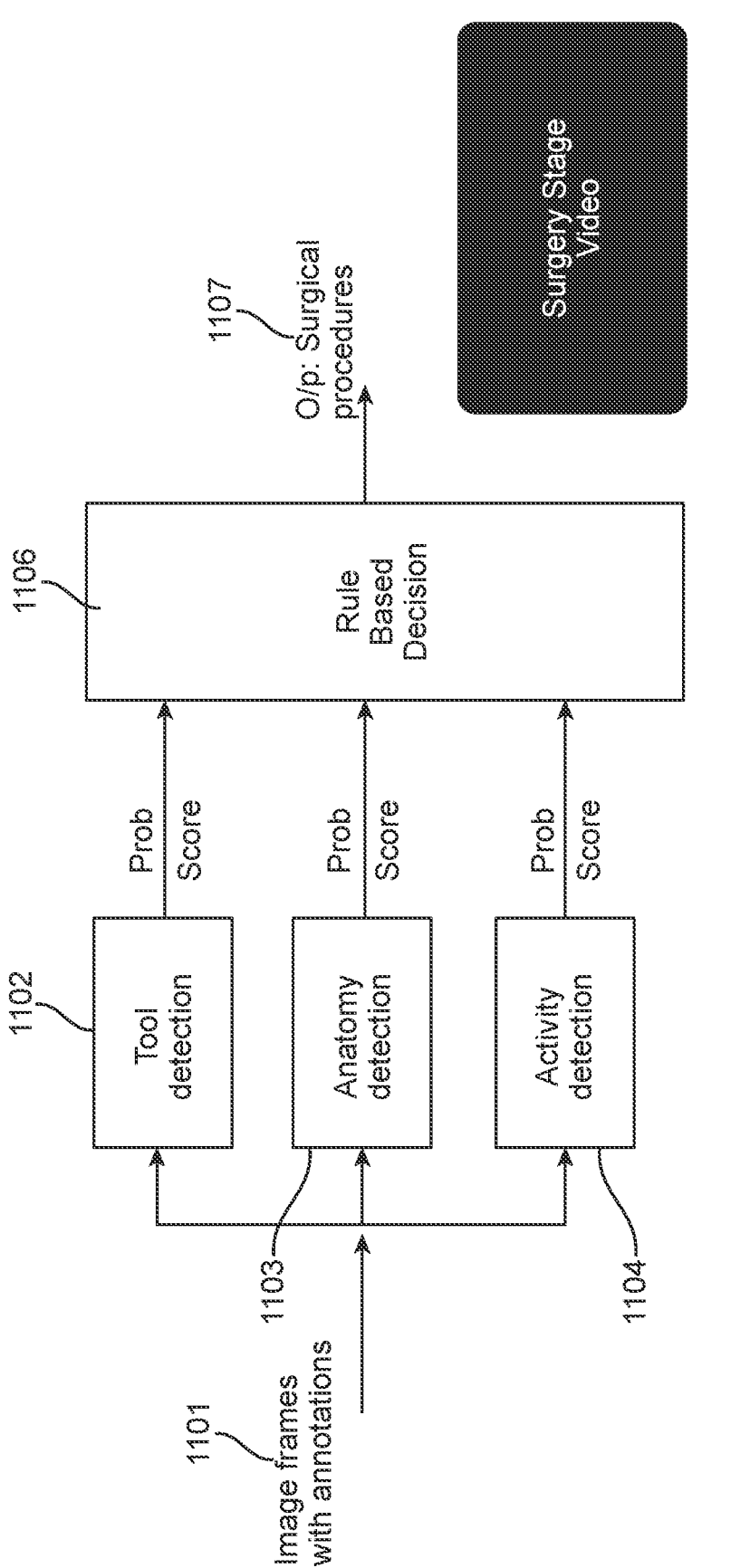
FIG. 11A shows another example of the process of identifying a surgical procedure, according to some embodiments.

FIG. 11A shows another example of the process of identifying a surgical procedure, as described herein. Image frames with annotations 1101 may be received and segmented into one or more segments using one or more classifier models. The classifier models may comprise a tool recognition model 1102, an anatomy detection model 1103, and/or an activity detection model 1104. The outputs from the one or more classifiers may be processed and combined using a rule-based decision algorithm 1106. A predicted surgical procedure 1107 may be provided as a label overlaid on the surgical video stream.

Figure 11B:
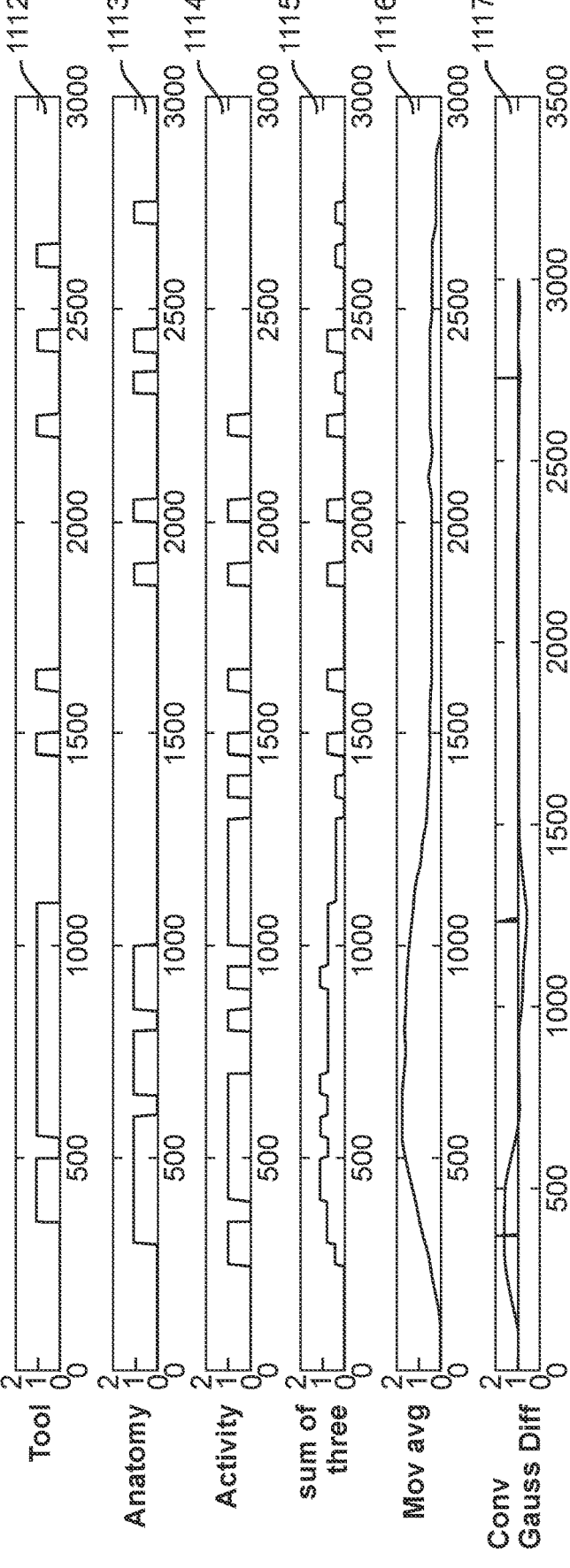
FIG. 11B shows an example of an output from tool detection, anatomy detection, and activity detection models across time, according to some embodiments.

FIG. 11B shows an example of an output from each of the components across time (e.g., duration of a procedure), described herein. The output shown in FIG. 11B may comprise a movement of the recognized tool, anatomy, and/or a change in the activity. The movement of a tool may be due to the movement of the camera or a change on the procedure, where a tool is swapped. The movement in the anatomy may be due the structural changes in the anatomy due, for example, to the procedure or due to the movement of the camera. In some embodiments, the operator may pause or change an activity during the procedure and resume the action after the pause. An example of an output from the tool recognition model 1102 (e.g., a movement of a recognized tool) is shown in graph 1112; an example of an output from the anatomy detection model 1103 (e.g., a movement of a recognized anatomy) is shown in graph 1113; and an example of an output from the activity detection model 1104 (e.g., a pause or change in the activity or the surgical procedure) is shown in graph 1114. To generate a seamless labeling of the predicted procedure, the outputs from the tool recognition model 1102, the anatomy detection model 1103, and/or the activity detection model 1104 are combined (e.g., summed) as shown in graph 1115. In some embodiments, the sum of the outputs is averaged over time to generate an averaged sum as shown in graph 1116. In some embodiments, the average sum is processed using a smoothing algorithm to generate a smooth average sum. The smoothing algorithm may comprise a gaussian smoothing function. The smoothing algorithm may comprise a convolutional neural network (e.g., convolutional neural network) with its activity shown in graph 1117.

Figure 12:
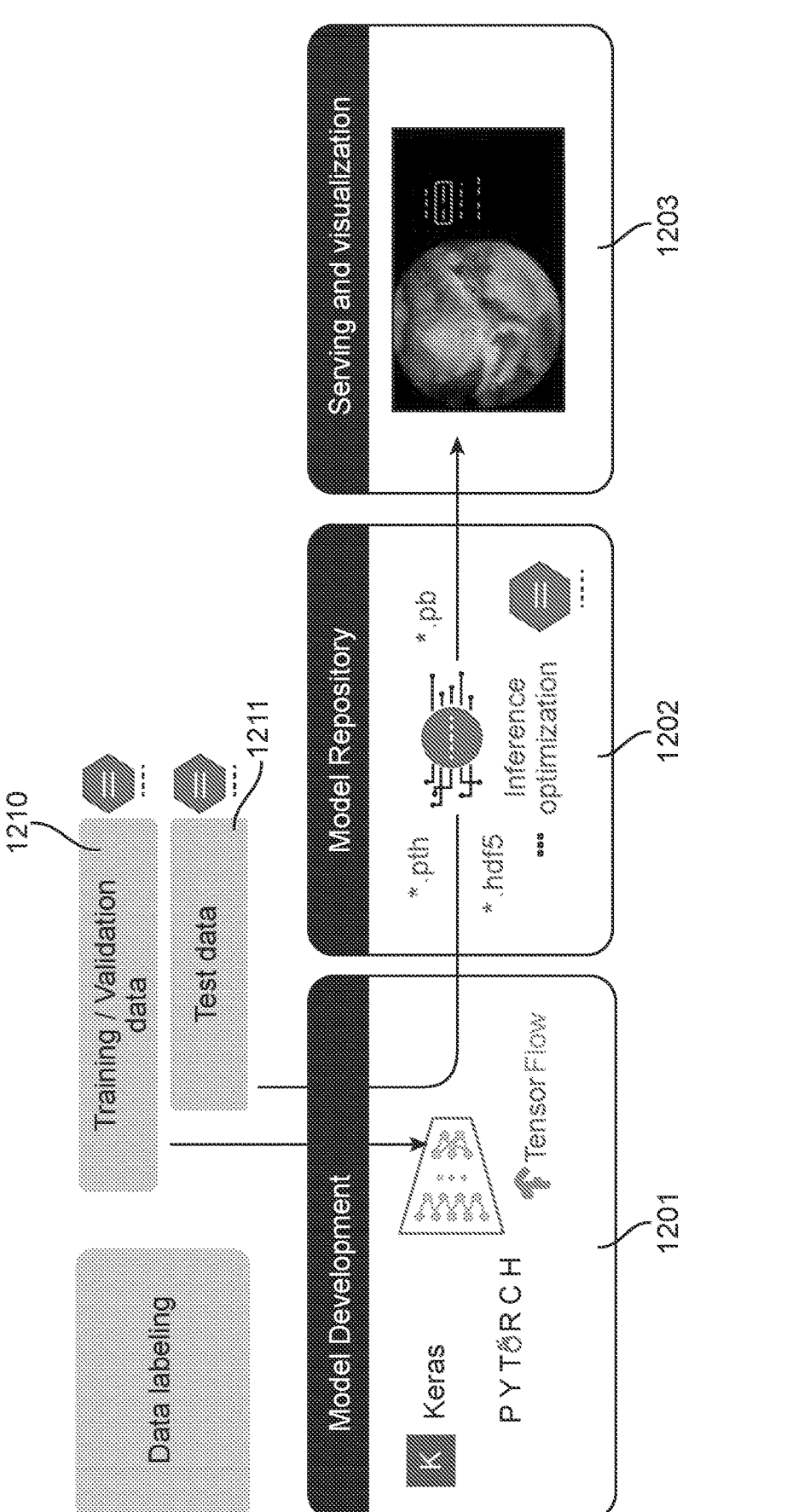
FIG. 12 shows a schematic diagram of elements in an AI assisted surgery system, according to some embodiments.

FIG. 12 shows a schematic diagram of exemplary elements in AI assisted surgery methods and systems, described herein. The systems and methods may comprise elements comprising model development 1201, model repository 1202, and providing (e.g., visualizing) a label or mask 1203. Developing AI/machine learning models or algorithms used to process a surgical image may comprise training and/or validation steps 1210. Test data 1211 may be used to train and validate AI/machine learning models. A feature identified/recognized in an image obtained from a surgery (e.g., a frame of a surgical video) may be visualized (e.g., a mask, or a label) overlaid 1203 on a video or image of the surgical field of view.

Computer Systems

Figure 5:
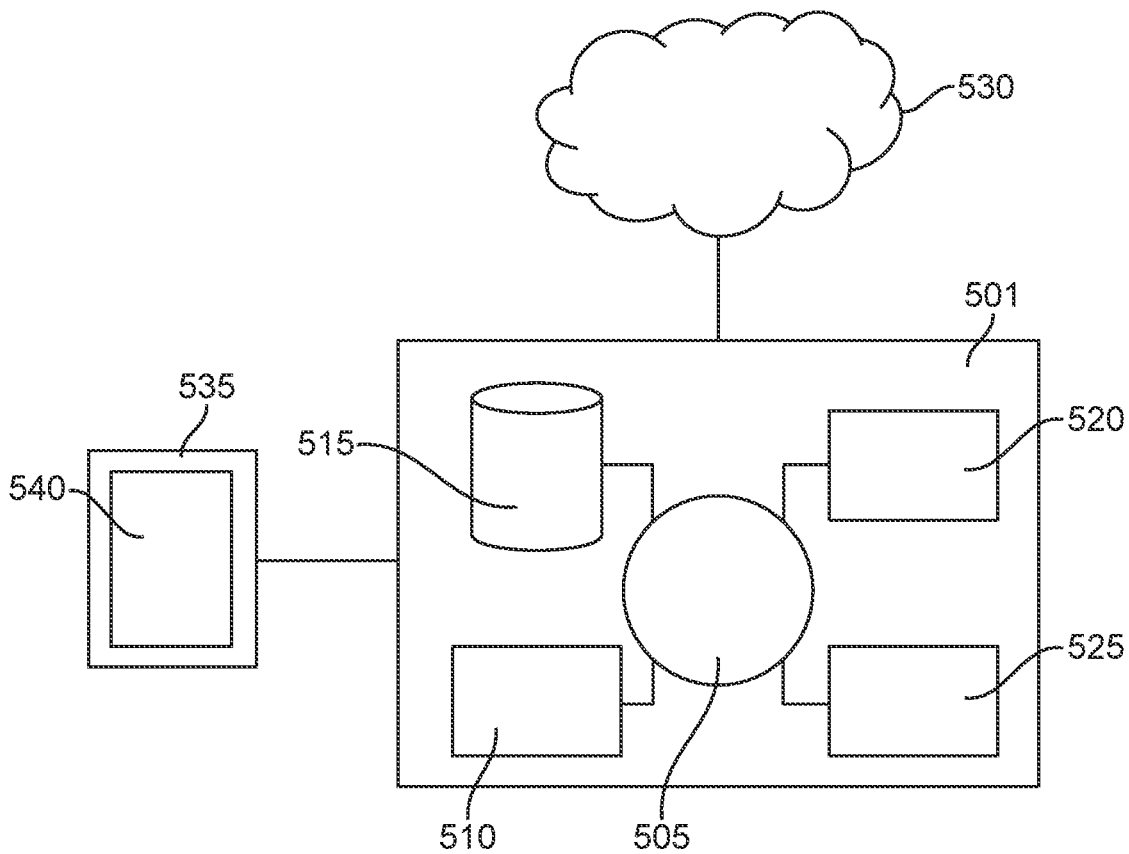
FIG. 5 shows a computer system that is programmed or otherwise configured to implement methods provided herein, according to some embodiments.

Various embodiments of the invention also provide computer systems that are programmed to implement methods of the invention. Accordingly, a description of one or more embodiments of such computer systems will now be described. FIG. 5 shows a computer system 501 that is programmed or otherwise configured to perform one or more functions or operations of methods of the present invention. The computer system 501 can regulate various aspects of the present invention, such as, for example, of receiving an image from an interventional imaging device, identifying features in the image using an image recognition algorithm, overlaying the features on a video feed on a display device, make recommendations or suggestion to an operator based on the identified features in the image. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some embodiments is a telecommunication and/or data network. The network 530 can include one or more computer servers, which can enable distributed computing, such as cloud computing. The network 530, in some embodiments with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present invention. Examples of operations performed by the CPU 505 can include fetch, decode, execute, and writeback.

The CPU 505 can be part of a circuit, such as an integrated circuit. One or more other components of the system 501 can be included in the circuit. In some embodiments, the circuit is an application specific integrated circuit (ASIC).

The storage unit 515 can store files, such as drivers, libraries and saved programs. The storage unit 515 can store user data, e.g., user preferences and user programs. The computer system 501 in some embodiments can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., a portable computer, a tablet, a smart display device, a smart tv, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. In one or more embodiments, the machine executable or machine-readable code can be provided in the form of software. During use, the code can be executed by the processor 505. In some embodiments, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, an overlay of the identified features on a video feed from an arthroscope or to provide a recommendation to an operator in the course of a surgery. Examples of UI's include, without limitation, a graphical user interface (GUI) and web-based user interface.

Methods and systems of the present invention can be implemented by way of one or more algorithms. An algorithm can be implemented by way of software upon execution by the central processing unit 505. The algorithm can, for example, receiving an image from an interventional imaging device, identifying a feature in the image using an image recognition algorithm, overlaying the features on a video feed on a display device, make recommendations or suggestion to an operator based on the identified feature in the image.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be further understood that various alternatives to the embodiments of the invention described herein may be employed in practicing the invention. Accordingly, it should be understood that the invention covers various alternatives, modifications, variations or equivalents to the embodiments of the invention described herein.

Also, elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Further, embodiments of the invention specifically contemplate the exclusion of an element, act, or characteristic, etc. when that element, act or characteristic is positively recited. Hence, the scope of the present invention is not limited to the specifics of the described embodiments but is instead limited solely by the appended claims.

What is claimed is:

1. A system for implementing a hierarchical pipeline for guiding a minimally invasive procedure, the system comprising one or more computer processors and one or more non-transitory computer-readable storage media storing instructions that are operable, when executed by said one or more computer processors, to cause said one or more computer processors to perform operations comprising:

receiving at least one image captured by an interventional imaging device;

identify, by at least one upstream module, one or more image features of a region of treatment or a portal of entry in the at least one image based on said at least one upstream module, wherein said at least one upstream module comprises a first trained image processing algorithm;

transferring the received image to a first downstream module to identify one or more image features of a pathology in the at least one image identified by the at least one upstream module, wherein said first downstream module comprises a second trained image processing algorithm;

transferring the received image to a second downstream module to identify one or more image features of a surgical tool, a surgical tool element, an operational procedure or action relating to said minimally invasive procedure in the at least one image identified by the at least one upstream module, wherein said second downstream module comprises a third trained image processing algorithm;

labeling said one or more image features identified by the upstream module, the first downstream module, and the second downstream module;

displaying said labeled one or more image features identified by the upstream module, the first downstream module, and the second downstream module in said at least one image continuously to an operator in the course of said minimally invasive procedure; and discarding the received image when the at least one upstream module fails to identify one or more image features of a region of treatment in the at least one received image.

2. The system of claim 1, wherein activating the first downstream module is independent from activating the second downstream module.

3. The system of claim 1, wherein said first, second, or third trained image processing algorithms comprise at least a machine learning algorithm, a deep learning algorithm, or a combination of both and is trained using at least one training dataset.

4. The system of claim 3, wherein said training dataset is configured for a shoulder surgery or for a knee surgery.

5. The system of claim 3, wherein said training dataset comprises a plurality of training images comprising one or more surgical procedures, surgical tools, surgical tool elements, anatomical structures, or pathologies.

6. The system of claim 5, wherein said first, second, or third trained image processing algorithms further comprise a plurality of augmentation techniques performed on the training images.

7. The system of claim 6, wherein said augmentation techniques comprise rotating said training images.

8. The system of claim 6, wherein said augmentation techniques comprise flipping said training images along a vertical axis.

9. The system of claim 6, wherein said augmentation techniques comprise enlarging or cropping said training images.

10. The system of claim 1, wherein said first, second, or third trained image processing algorithms store said displayed images with labeled features in a memory device.

11. The system of claim 1, wherein said first, second, or third trained image processing algorithms discard said displayed images with labeled features to minimize memory usage.

12. A method for implementing a hierarchical pipeline for guiding a minimally invasive procedure, the method comprising:

receiving at least one image captured by an interventional imaging device;

identify, by at least one upstream module, one or more image features of a region of treatment or a portal of entry in the at least one image based on said at least one upstream module, wherein said at least one upstream module comprises a first trained image processing algorithm;

transferring the received image to a first downstream module to identify one or more image features of a pathology in the at least one image identified by the at least one upstream module, wherein said first downstream module comprises a second trained image processing algorithm;

transferring the received image to a second downstream module to identify one or more image features of a surgical tool, a surgical tool element, an operational procedure or action relating to said minimally invasive procedure in the at least one image identified by the at least one upstream module, wherein said second downstream module comprises a third trained image processing algorithm;

labeling said one or more image features identified by the upstream module, the first downstream module, and the second downstream module;

displaying said labeled one or more image features identified by the upstream module, the first downstream module, and the second downstream module in said at least one image continuously to an operator in the course of said minimally invasive procedure; and discarding the received image when the at least one upstream module fails to identify one or more image features of a region of treatment in the at least one received image.

13. The method of claim 12, wherein activating the first downstream module is independent from activating the second downstream module.

14. The method of claim 12, wherein said first, second, or third trained image processing algorithms comprise a machine learning or a deep learning algorithms and is trained using at least one training dataset.

15. The method of claim 14, wherein said training dataset is configured for a shoulder surgery or for a knee surgery.

16. The method of claim 14, wherein said training dataset comprises a plurality of training images comprising one or more surgical procedures, surgical tools, surgical tool elements, anatomical structures, or pathologies.

17. The method of claim 14, wherein the first, second, or third trained image processing algorithms further include a plurality of augmentation techniques.

18. The method of claim 17, wherein said augmentation techniques comprise rotating said training images.

19. The method of claim 17, wherein said augmentation techniques comprise flipping said training images along a vertical axis.

20. The method of claim 17, wherein said augmentation techniques comprise enlarging or cropping said training images.

21. The method of claim 12, wherein said first, second, or third trained image processing algorithms store said displayed images with labeled features in a memory device.

22. The method of claim 12, wherein said first, second, or third trained image processing algorithms discard said displayed images with labeled features to minimize memory usage.

* * * * *